(12) United States Patent
Kojima et al.

(10) Patent No.: US 8,634,108 B2
(45) Date of Patent: Jan. 21, 2014

(54) METHOD AND APPARATUS FOR INSPECTING IMAGE, IMAGE FORMING APPARATUS, AND COMPUTER-READABLE RECORDING MEDIUM STORING IMAGE INSPECTING PROGRAM

(75) Inventors: Keiji Kojima, Kanagawa (JP); Fumihiro Nakashige, Kanagawa (JP); Hitoshi Itoh, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 315 days.

(21) Appl. No.: 13/064,959

(22) Filed: Apr. 28, 2011

(65) Prior Publication Data

US 2011/0273732 A1 Nov. 10, 2011

(30) Foreign Application Priority Data

May 10, 2010 (JP) .................................. 2010-108198

(51) Int. Cl.
*H04N 1/40* (2006.01)
(52) U.S. Cl.
USPC .......................................... 358/2.1; 358/468
(58) Field of Classification Search
USPC ........... 358/1.9, 2.1, 468, 509–510, 475, 400, 358/500, 406, 504
See application file for complete search history.

(56) References Cited

U.S. PATENT DOCUMENTS

| 7,139,511 | B2 | 11/2006 | Ishibashi |
| 2003/0007814 | A1 | 1/2003 | Richards |
| 2009/0196641 | A1 | 8/2009 | Banton et al. |

FOREIGN PATENT DOCUMENTS

| JP | 2004354624 A | 12/2004 |
| JP | 2005277678 A | 10/2005 |

OTHER PUBLICATIONS

Extended European Search Report dated Jun. 8, 2012.

*Primary Examiner* — Thomas D Lee
*Assistant Examiner* — Stephen M Brinich
(74) *Attorney, Agent, or Firm* — Harness, Dickey & Pierce, P.L.C.

(57) ABSTRACT

An image inspecting apparatus includes a first light illuminating unit that irradiates a measured object on which an image is formed with illuminating light from a diagonal direction; an imaging unit that receives specular light of the illuminating light with which the measured object is irradiated by the first light illuminating unit; and an image inspecting unit that inspects the image. The image inspecting unit generates gloss reference data from density distribution data included in print data used for forming the image by using a converting unit. The image inspecting unit inspects a gloss distribution of the image by using the gloss reference data and a gloss distribution of the image that is generated based on an amount of the specular light received by the imaging unit.

16 Claims, 21 Drawing Sheets

METHOD AND APPARATUS FOR INSPECTING IMAGE, IMAGE FORMING APPARATUS, AND COMPUTER-READABLE RECORDING MEDIUM STORING IMAGE INSPECTING PROGRAM

BACKGROUND OF THE INVENTION

1. Field of the Invention

The present invention relates to a method and an apparatus for inspecting a measured object on which an image is formed, an image forming apparatus including the image inspecting apparatus, and a computer-readable recording medium storing an image inspecting program.

2. Description of the Related Art

In an electrophotographic image forming apparatus, a toner image formed on a sheet of paper as an image carrying medium is fixed onto the sheet by melting the toner by a thermal fusing unit in a step called "fusing". Thus, the gloss of the fused toner image may be varied depending on the amount of toner attached onto the sheet. In such an image forming apparatus, the type of the sheet as an output image base may be varied. For example, the fusing condition of the sheet with respect to the toner varies depending on the thermal capacity of the sheet, resulting in variations in the gloss of the fused toner image. Also, when the gloss of the sheet itself is varied, the gloss of the toner image formed on the sheet varies.

Various attempts have been made to improve image quality in terms of gloss. For example, the gloss of the toner image may be varied by controlling the fusing unit in accordance with user demand. A transparent toner may be used to actively impart gloss to the output image. Further, an image may be formed on a high-gloss sheet.

However, even when the toner is attached onto the sheet accurately with an intended toner amount distribution, the fused condition of the toner on the sheet may become uneven, resulting in the appearance of lines, due to a problem in the fusing unit. Specifically, visible lines called "fusing lines" may appear when the fused sheet is observed at an angle, although there is little variation in the density distribution. Such an image is determined to be defective.

As an output image inspecting apparatus, an image inspecting apparatus may be considered that is capable of inspecting the output image from an electrophotographic image forming apparatus on an on-demand basis. Desirably, such an image inspecting apparatus is capable of measuring not just the density distribution of an entire area of an output image but also its gloss distribution.

The gloss of an object may be measured by illuminating the object with illuminating light at a certain incident angle and then measuring the intensity of specular light reflected from the measured object. In this case, because the specular light is measured, the incident angle and the reflected angle are the same, and these angles may be set depending on the measured object. The density of an area of the object may be measured by illuminating the area of the measured object with illuminating light from a direction such that no specular reflection is caused, and measuring the intensity of diffused reflected light reflected from the area.

A technology for inspecting a gloss distribution is discussed in Japanese Laid-open Patent Publication No. 2005-277678. In this technology, gloss inspection is performed on the assumption that, when image data read from a read area in the direction of diffused reflected light provide substantially the same value, the read area has substantially the same density, and that, if there is gloss abnormality in the read area, a difference will be caused in the image output of the read area based on the image data read in the direction of specular light. Namely, the technology assumes that the gloss is the same when the density is the same.

However, even when the image density is the same, the amount of toner attached ("attached toner amount") may vary depending on the density of the colorant of the toner or the toner size. It is also known that the gloss of a fused image may vary depending on the toner attached amount. Further, when gray levels of an image, such as a natural image, are formed by superposition of halftone dot images of plural colors of toner, such as cyan, magenta, and yellow, each of the image-forming colors has a density distribution. Thus, the gloss distribution of the overall image varies depending on the toner attached amount regardless of the image-forming color.

Specifically, rather than the toner attached amount of each individual color, a total value of the attached amounts of the plural colors of toners is important. This means that, even when the image density is the same, the toner attached amount may vary, and therefore the gloss may also vary. Thus, the relationship that dictates that when the image density is the same, the gloss is the same does not hold. In other words, a gloss distribution cannot be accurately inspected solely based on the relationship between image density and gloss.

SUMMARY OF THE INVENTION

In one aspect of the invention, an image inspecting apparatus includes a first light illuminating unit configured to irradiate a measured object on which an image is formed with illuminating light from a diagonal direction; an imaging unit configured to receive specular light of the illuminating light with which the measured object is irradiated by the first light illuminating unit; and an image inspecting unit configured to inspect the image. The image inspecting unit generates gloss reference data from density distribution data included in print data used for forming the image, by using a converting unit. The image inspecting unit inspects a gloss distribution of the image by using the gloss reference data and a gloss distribution of the image generated based on an amount of the specular light received by the imaging unit.

In another aspect, an image inspecting method includes a first light illuminating step of irradiating a measured object on which an image is formed with illuminating light from a diagonal direction; an imaging step of receiving specular light of the illuminating light with which the measured object is irradiated by the first light illuminating step; and an image inspecting step of inspecting the image. The image inspecting step includes generating gloss reference data from density distribution data included in print data used for forming the image, by using a converting unit, and inspecting a gloss distribution of the image by using the gloss reference data and a gloss distribution of the image that is generated based on an amount of the specular light received in the imaging step.

In another aspect, an image forming apparatus for forming an image on an image carrying medium includes the image inspecting apparatus configured to inspect one or both of a gloss distribution and a density distribution of the image carrying medium as the measured object on which the image is formed.

In another aspect, a non-transitory computer-readable recording medium stores a program that causes a computer to perform the image inspecting method.

DETAILED DESCRIPTION OF THE PREFERRED EMBODIMENTS

Figure 1:
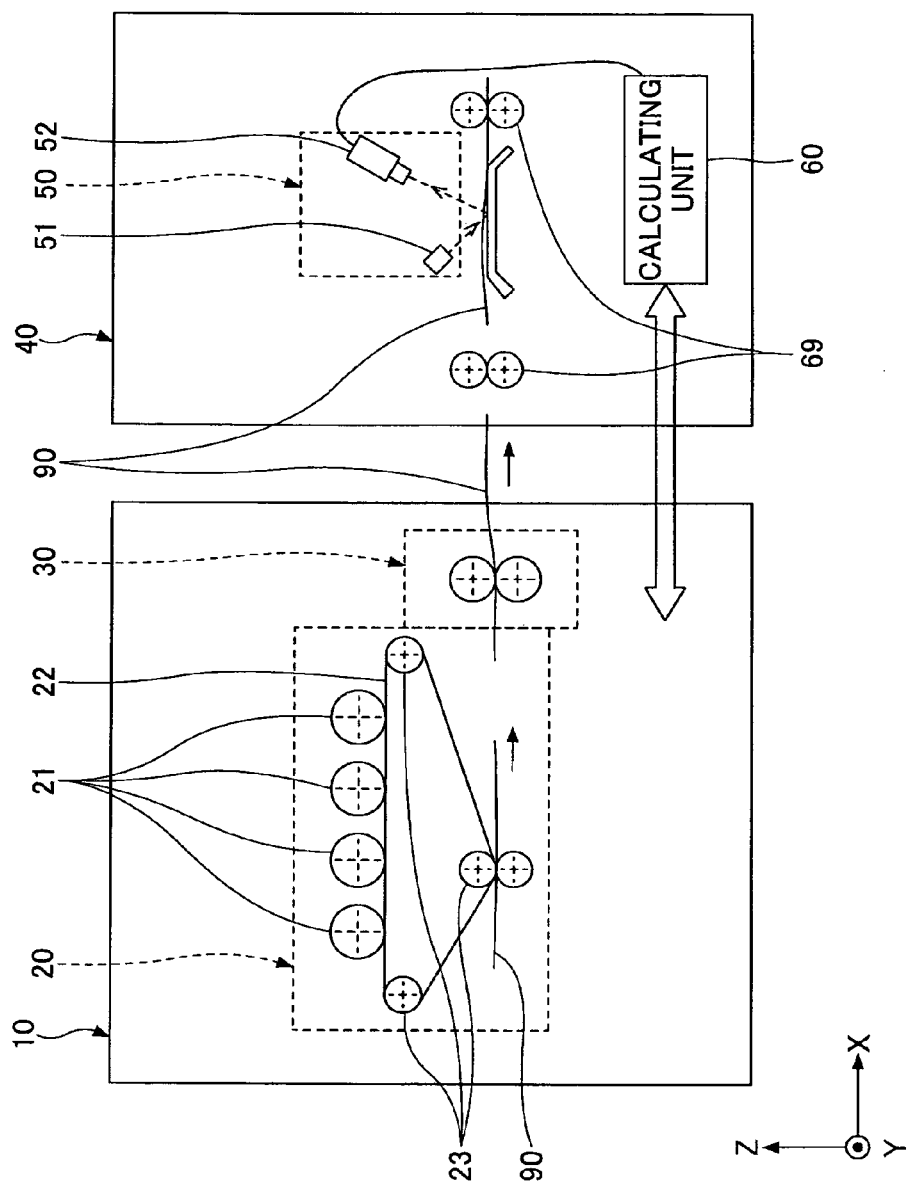
FIG. 1 illustrates an image inspecting apparatus according to a first embodiment of the present invention.

Embodiments of the present invention are described with reference to the attached drawings, wherein like reference numerals designate identical or corresponding parts throughout the several views.

<First Embodiment>

FIG. 1 illustrates an image inspecting apparatus 40 according to a first embodiment of the present invention. The image inspecting apparatus 40 is connected with an image forming apparatus 10. The image forming apparatus 10 includes an image forming unit 20 and a fusing unit 30. The image forming unit 20 includes photosensitive members 21, an intermediate transfer unit 22, and a transporting members 23. Numeral 90 designates an image carrying medium as a measured object, which may include a sheet of paper.

The image inspecting apparatus 40 includes a gloss measuring unit 50, a calculating unit 60, and a transporting unit 69. The gloss measuring unit 50 includes a gloss illuminating device 51 and an imaging device 52. Preferably, an imaging lens may be provided in front of the imaging device 52.

The gloss illuminating device 51 of the gloss measuring unit 50 illuminates a read area of the image carrying medium 90 (such as a line on the image carrying medium 90 in a Y direction) with illuminating light at a predetermined incident angle. The gloss illuminating device 51 may include plural light-emitting elements disposed side by side in a direction (Y direction) parallel to the read area of the image carrying medium 90. The light-emitting elements may include LEDs (Light Emitting Diodes) or organic EL (Electro-Luminescence) elements. Compared to a fluorescent light, an LED has high light-emitting directionality, so that it produces little outgoing light in directions other than an intended direction, resulting in less flaring light. Thus, LEDs may be suitably used as the light-emitting elements for the present embodiment. The gloss illuminating device 51 is an example of a light illuminating unit according to the present embodiment.

The number of the light-emitting elements of the gloss illuminating device 51 is not particularly limited. Preferably, the light-emitting elements are disposed closely next to each other so that they can produce the illuminating light for obtaining specular light from the entire read area of the image carrying medium 90. The "specular light" refers to the reflected light reflected from the read area of the image carrying medium 90 in a direction away from the incident direction of the illuminating light and with the same incident angle as that of the incident light. The "diffused reflected light" refers to reflected light other than the specular light.

The imaging device 52 of the gloss measuring unit 50 includes plural pixels disposed side by side in a direction (Y direction) parallel to the read area of the image carrying medium 90. The imaging device 52 obtains the amount of the specular light from the read area of the image carrying medium 90. Namely, the imaging device 52 is disposed at a position such that the imaging device 52 can image the specular light from the read area. By turning on the gloss illuminating device 51 and acquiring the amount of the specular light with the imaging device 52, data indicating a gloss distribution of the read area (one line) of the image carrying medium 90 can be acquired.

The imaging device 52 may include a MOS (Metal Oxide Semiconductor) device, a CMOS (Complimentary Metal Oxide Semiconductor) device, a CCD (Charge Coupled Device), or a CIS (Contact Image Sensor). When the measured object includes a color image, an imaging device of a 3 line type that is sensitive to each of the RGB colors may be used. The imaging device 52 is an example of an imaging unit of the image inspecting apparatus 40 according to the present embodiment.

The calculating unit 60 inspects an output image formed on the image carrying medium 90 based on image data (i.e., print data used by the image forming apparatus 10 when forming the output image on the image carrying medium 90) obtained from the image forming apparatus 10 and the gloss distribution of the output image on the image carrying medium 90 that is actually measured by the gloss measuring unit 50.

The calculating unit 60 may include a CPU and a memory unit such as a ROM and a RAM, which are not illustrated. One of the memory units (not illustrated) of the calculating unit 60 may store a program for inspecting the gloss distribution of the measured object. The various functions of the calculating unit 60 may be realized upon execution of the program by the CPU (not illustrated). The program for inspecting a gloss distribution may be stored in a computer-readable recording medium, such as an optical computer-readable recording medium or a magnetic computer-readable recording medium. The calculating unit 60 is an example of an image inspecting unit of the image inspecting apparatus 40 according to the present embodiment.

The transporting unit 69 transports the image carrying medium 90 in an X direction indicated in FIG. 1. After the gloss illuminating device 51 is turned on and the data of the gloss distribution for one line (one-dimension) is acquired, the image carrying medium 90 is transported by the transporting unit 69 in the X direction by a predetermined distance. Thereafter, the gloss distribution for the next one line (one-dimension) is acquired. By repeating this operation, the gloss distribution of the entire (two-dimensional) area of the image carrying medium 90 can be acquired.

A toner image formed by the image forming unit 20 of the image forming apparatus 10 is fused onto the image carrying medium 90 by the fusing unit 30, forming an output image on the image carrying medium 90. The output image on the image carrying medium 90 is then fed into the image inspecting apparatus 40. In the image inspecting apparatus 40, the gloss distribution is acquired by the gloss measuring unit 50 while the image carrying medium 90 is transported by the transporting unit 69. The gloss distribution data is inspected by the calculating unit 60.

Figure 2:
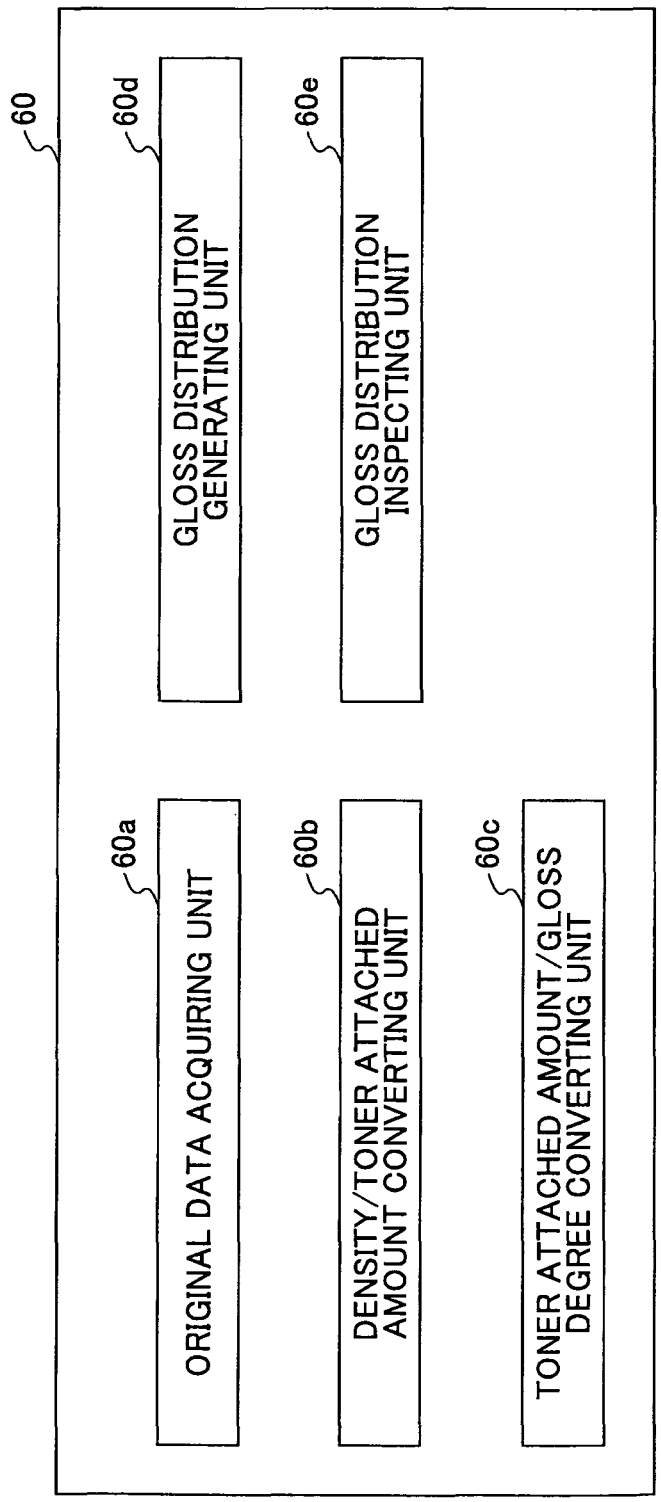
FIG. 2 is a functional block diagram of an image inspecting unit calculating unit according to the first embodiment.
Figure 3:
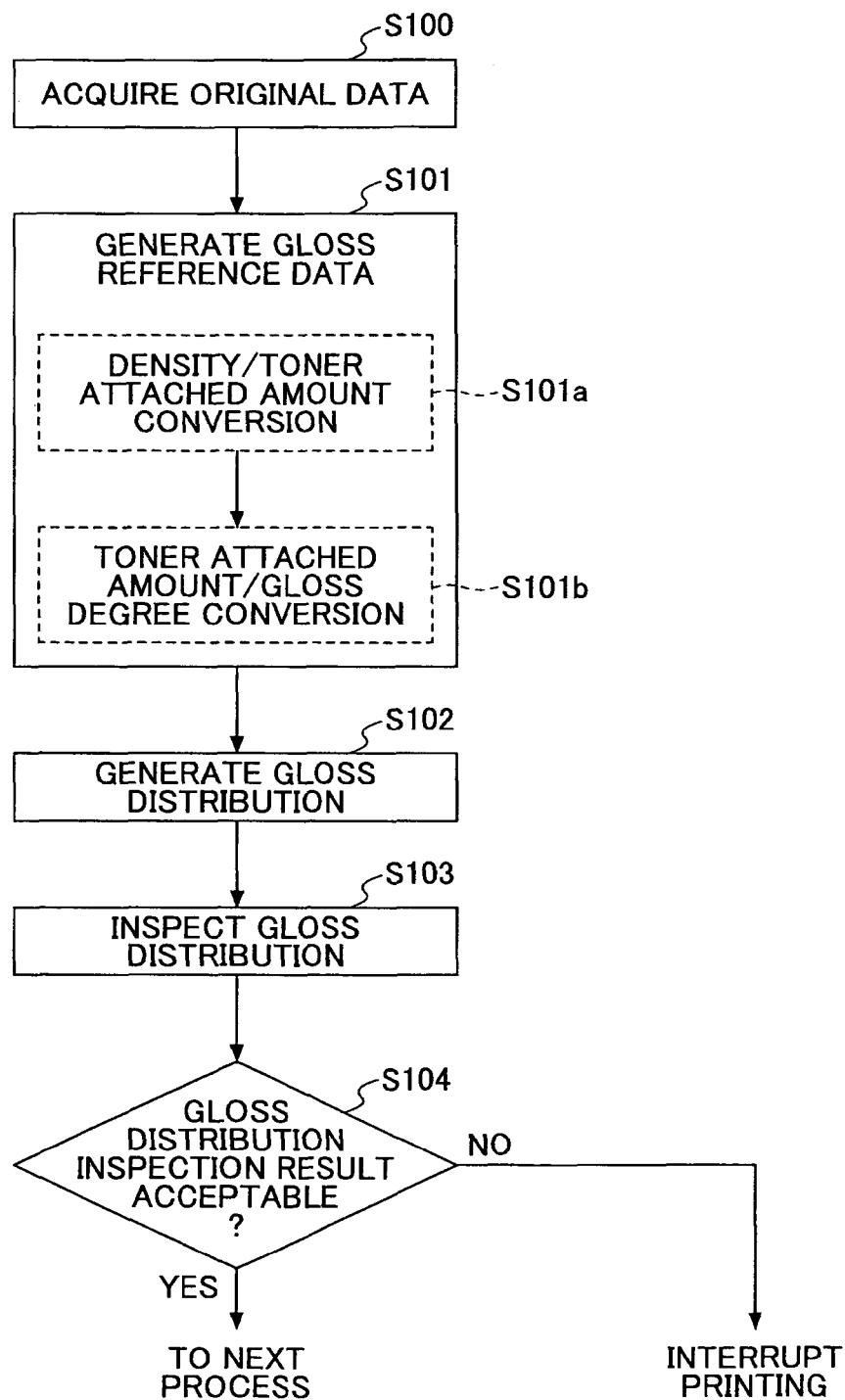
FIG. 3 is a flowchart of a gloss distribution inspection process performed by the calculating unit of the first embodiment.

FIG. 2 is a functional block diagram of the calculating unit 60. FIG. 3 is a flowchart of a gloss distribution inspection process performed by the calculating unit 60. With reference to FIGS. 2 and 3, the gloss distribution inspection process is described.

In step S100, a original data acquiring unit 60a of the calculating unit 60 acquires density distribution data included in the print data used by the image forming apparatus 10 in forming the output image on the carrying medium 90.

Figure 4:
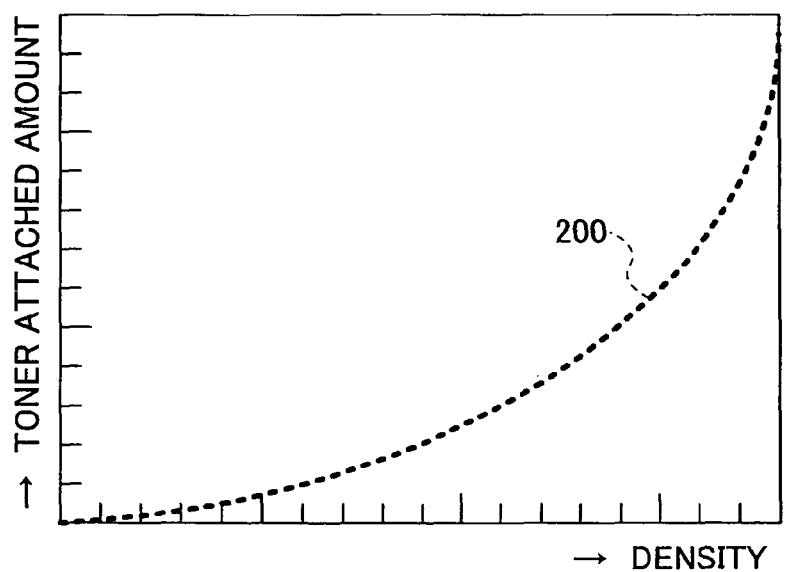
FIG. 4 is a density/toner attached amount conversion chart.

In step S101, a density/toner attached amount converting unit 60b and a toner attached amount/gloss degree converting unit 60c of the calculating unit 60 generate gloss reference data. Specifically, in step S101a, the density/toner attached amount converting unit 60b converts the density distribution data included in the print data acquired in step S100 into a toner attached amount on a pixel by pixel basis by using a density/toner attached amount conversion chart 200 illustrated in FIG. 4. The density/toner attached amount conversion chart 200 may be designed in accordance with the type of toner used in the image forming apparatus 10. This is due to the fact that the toner attached amount may vary even when the toner density is the same, depending on the density of colorant in the toner or the toner size.

Figure 5:
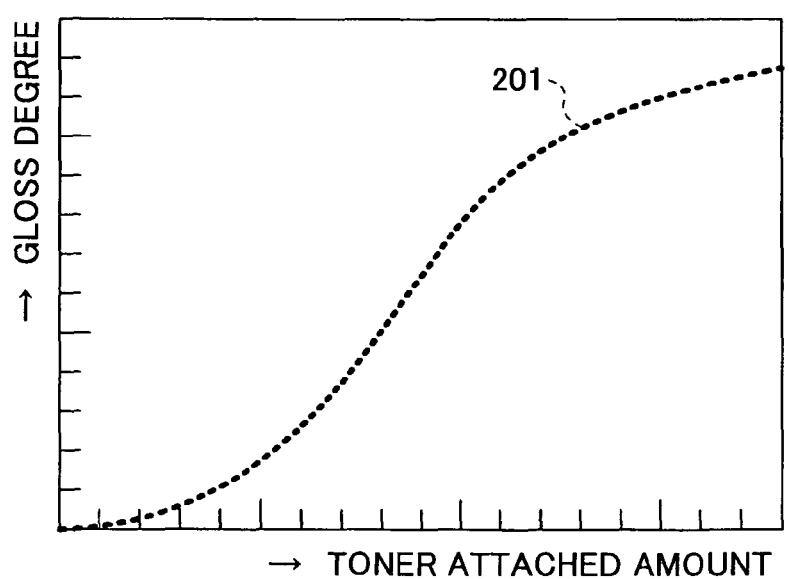
FIG. 5 is a first example of a toner attached amount/gloss degree conversion chart.
Figure 6:
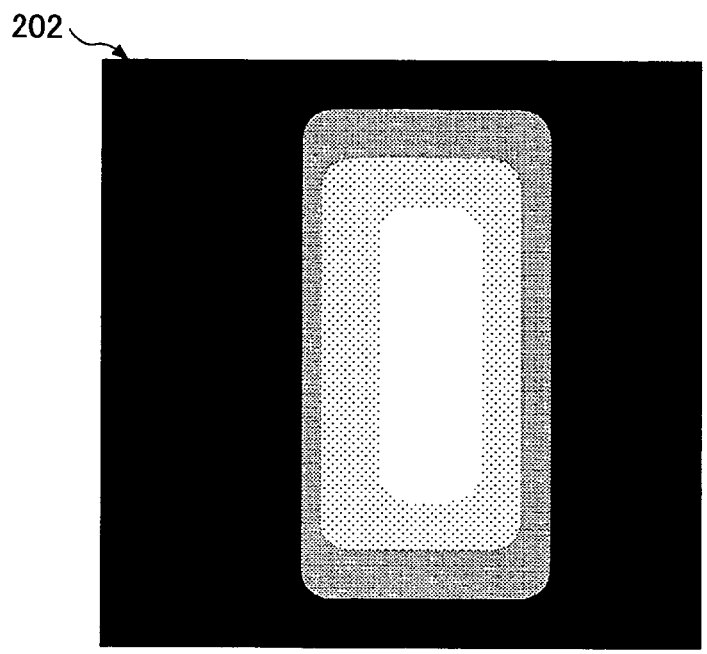
FIG. 6 is a first example of gloss reference data.

In step S101b, the toner attached amount/gloss degree converting unit 60c converts the toner attached amount obtained in step S101a into a gloss degree on a pixel by pixel basis by using a toner attached amount/gloss degree conversion chart 201 illustrated in FIG. 5, thereby generating gloss reference data 202 illustrated in FIG. 6. The toner attached amount/ gloss degree conversion chart 201 is a table for calculating a target gloss degree from the toner attached amount. The toner attached amount/gloss degree conversion chart 201 may be designed in accordance with the toner used in the image forming apparatus 10 and the characteristics of the fusing unit 30. This is due to the fact that the gloss degree of an image may vary even when the toner attached amount is the same, depending on the amount or type of a wax component of the toner used, or the fusing temperature.

The density/toner attached amount conversion chart 200 and the toner attached amount/gloss degree conversion chart 201 are examples of a converting unit according to the present embodiment. The form of the converting unit, however, is not limited to a table. Preferably, the converting unit may include conversion data, a conversion program, or a statistically or theoretically determined function.

Figure 7:
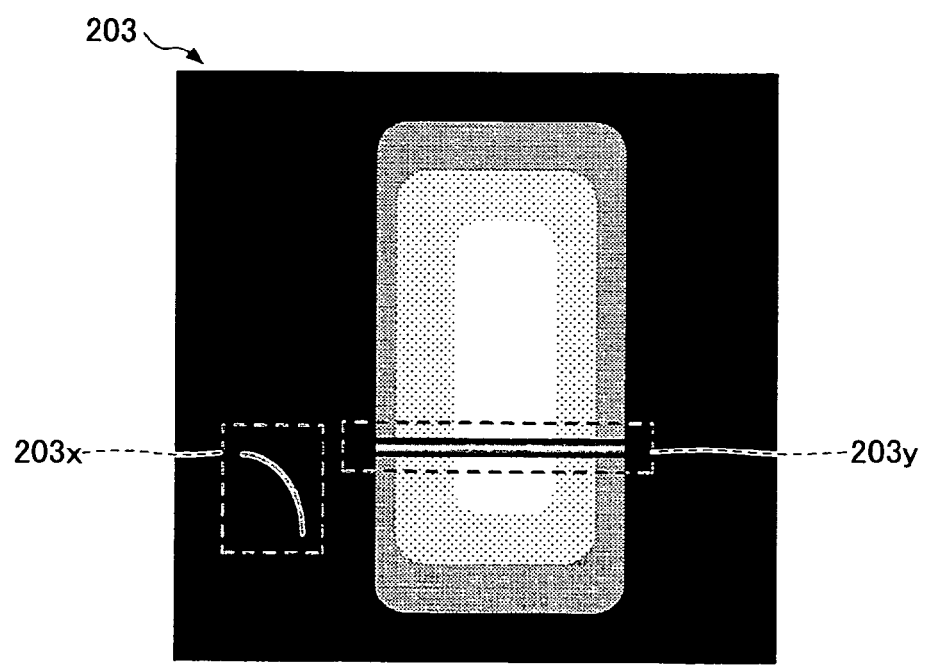
FIG. 7 is a first example of a gloss distribution of an output image formed on an image carrying medium.

In step S102, the gloss distribution generating unit 60d of the calculating unit 60 generates a gloss distribution 203 of the output image, as illustrated in FIG. 7 based on the gloss data of the output image formed on the image carrying medium 90 that is actually measured by the gloss measuring unit 50. Specifically, the gloss distribution generating unit 60d generates the gloss distribution 203 based on the amount of the specular light from the read area received by the imaging device 52.

The output image on the image carrying medium 90 that is actually measured by the gloss measuring unit 50 is formed by the image forming apparatus 10 based on the print data acquired in step S100. In the example of FIG. 7, the gloss distribution 203 generated by the gloss distribution generating unit 60d includes abnormal gloss portions 203x and 203y.

Figure 8:
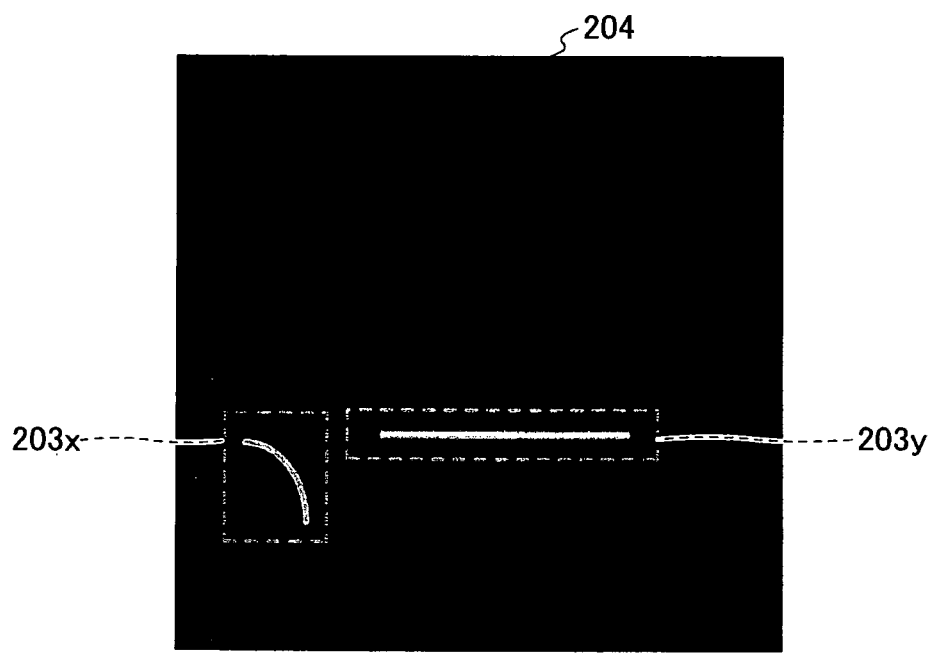
FIG. 8 illustrates a first example of a gloss distribution comparison result.

In step S103, a gloss distribution inspection unit 60e of the calculating unit 60 performs gloss distribution inspection. Specifically, the gloss distribution inspection unit 60e compares the gloss reference data 202 generated in step S101 with the gloss distribution 203 generated in step S102 on a pixel by pixel basis. Then, the gloss distribution inspection unit 60e generates a gloss distribution comparison result 204 (including the abnormal gloss portions 203x and 203y) illustrated in FIG. 8, based on differential data between the gloss reference data 202 and the gloss distribution 203 in terms of area or shape, for example.

In step S104, the gloss distribution inspection unit 60e determines the acceptability of the result of the gloss distribution inspection performed in step S103. Specifically, the gloss distribution inspection unit 60e determines the acceptability of the gloss distribution of the output data based on whether the gloss distribution comparison result 204 (including the abnormal gloss portions 203x and 203y) generated in step S103 is within a permissible range.

The determination of the acceptability of the gloss distribution may include a comparison of the gloss distribution comparison result 204 (including the abnormal gloss portions 203x and 203y) with comparison data stored in advance in a memory unit (not illustrated) of the calculating unit 60. When it is determined that the gloss distribution inspection result is acceptable ("YES" in S104), the process moves onto the next step. When the gloss distribution inspection result is determined to be not acceptable ("NO" in S104), the gloss distribution inspection unit 60e determines that there is an image quality problem in terms of gloss, and interrupts the printing operation (i.e., the forming of the output image on the image carrying medium 90) of the image forming apparatus 10. Preferably, step S104 may be omitted when it is not necessary to switch the process depending on the acceptability of the gloss distribution inspection result in step S103.

Thus, the calculating unit 60 determines the acceptability of a gloss distribution (gloss abnormality determination) during the image inspection of the output image formed on the image carrying medium 90 by the image forming apparatus 10. Preferably, the density/toner attached amount conversion chart 200 and the toner attached amount/gloss degree conversion chart 201 which are used during the image inspection by the calculating unit 60 may be integrated into a single density/ gloss degree conversion chart. This feature may be particularly effective when there is no need for switching the process depending on the toner attached amount, or when the capacity of the memory (not illustrated) of the calculating unit 60 is small. The density/gloss degree conversion chart is an example of a converting unit according to the present embodiment.

Thus, in accordance with the first embodiment, from density distribution data included in the print data used by the image forming apparatus in forming an output image on the image carrying medium, gloss reference data is generated by using a density/toner attached amount conversion chart and/or a toner attached amount/gloss degree conversion chart. As a result, the gloss distribution (gloss abnormality) of the measured object can be accurately inspected even in the absence of validity of the relationship that dictates that the gloss is the same when the image density is the same, on which relationship the related art is based.

For example, when the image density is the same, the gloss may be varied depending on the toner attached amount because the toner attached amount varies depending on the density of colorant in the toner or toner size. In this case, the gloss distribution (gloss abnormality) of the measured object can be accurately inspected in accordance with the present embodiment.

Further, gloss abnormality in the output image formed on the image carrying medium can be detected by a simple optical system. Even when the toner used in the image forming apparatus or the characteristics of the fusing unit are changed, the gloss distribution (gloss abnormality) of the measured object can be accurately measured by simply updating the density/toner attached amount conversion chart and/or the toner attached amount/gloss degree conversion chart.

Further, when multiple fusing condition control processes are performed in the image forming apparatus for gloss control purposes, the gloss distribution (gloss abnormality) of the measured object can be accurately inspected by simply modifying the toner attached amount/gloss degree conversion chart. Thus, the image inspecting apparatus 40 of the first embodiment is capable of inspecting the gloss distribution of the measured object.

<Second Embodiment>

Figure 9:
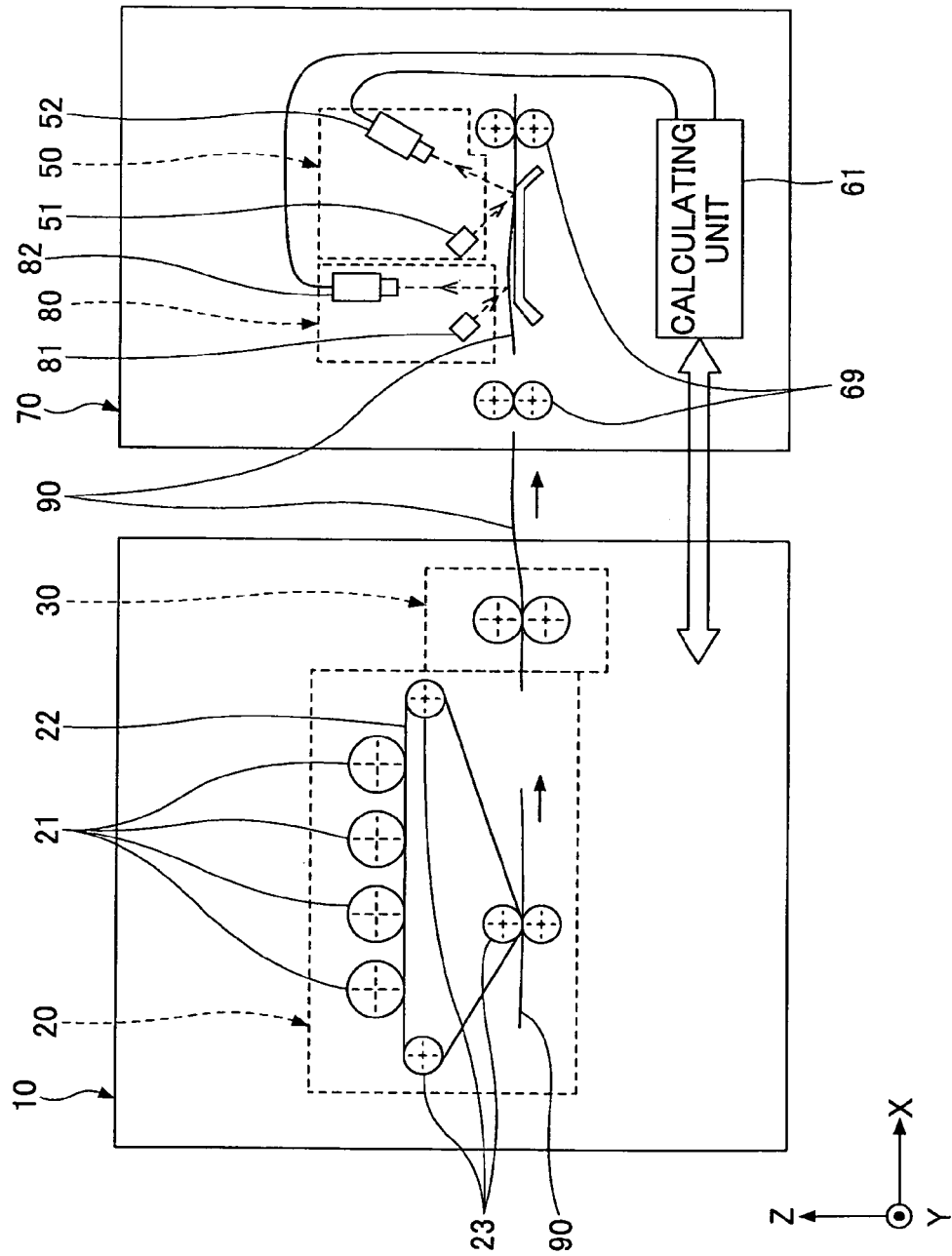
FIG. 9 illustrates an image inspecting apparatus according to a second embodiment of the present invention.

FIG. 9 illustrates an image inspecting apparatus 70 according to a second embodiment which is capable of inspecting a gloss distribution and a density distribution of a measured object. The image inspecting apparatus 70 is similar to the image inspecting apparatus 40 (FIG. 1) according to the first embodiment with the exception that a density measuring unit 80 including a density illuminating device 81 and an imaging device 82 is added and that the calculating unit 60 is replaced with a calculating unit 61. Preferably, an imaging lens may be disposed in front of the imaging device 82. In the following, the image inspecting apparatus 70 is described by mainly focusing on its difference from the image inspecting apparatus 40.

The density illuminating device 81 of the density measuring unit 80 irradiates the read area of the image carrying medium 90 with illuminating light at a predetermined incident angle. The predetermined incident angle may include any angle other than the incident angle of the gloss illuminating device 51; for example, the predetermined incident angle is 90°. Thus, the density illuminating device 81 illuminates the read area of the image carrying medium 90 with the illuminating light from a direction different from that of the gloss illuminating device 51. The density illuminating device 81 may include a diffused light illuminating unit using a xenon lamp or a LED array. The density illuminating device 81 is an example of a second light illuminating unit according to the present embodiment.

The imaging device 82 of the density measuring unit 80 may employ the same element as the imaging device 52. The imaging device 82 is disposed at a position enabling the imaging device 82 to image the diffused reflected light from the read area of the image carrying medium 90 that is irradiated by the density illuminating device 81. Thus, by turning on the density illuminating device 81 and acquiring the amount of the diffused reflected light from the read area with the imaging device 82, the density distribution of the read area (one line) of the image carrying medium 90 can be acquired. The imaging device 82 is an example of an imaging unit according to the present embodiment.

Preferably, the imaging device 82 may be combined with the imaging device 52 of the gloss measuring unit 50. For example, the gloss illuminating device 51 and the density illuminating device 81 may be appropriately disposed so that the single imaging device 52 can be provided for the gloss illuminating device 51 and the density illuminating device 81. Then, the gloss illuminating device 51 and the density illuminating device 81 may be alternately turned on so that the gloss distribution and the density distribution can be acquired alternately.

The calculating unit 61 inspects the output image on the image carrying medium 90 based on the image data (i.e., the print data used by the image forming apparatus 10 in forming the output image on the image carrying medium 90) acquired from the image forming apparatus 10 and the gloss distribution of the output image on the image carrying medium 90 that is actually measured by the gloss measuring unit 50. The calculating unit 61 also performs image inspection based on the image data acquired from the image forming apparatus 10 and the density distribution of the output image on the image carrying medium 90 that is actually measured by the density measuring unit 80.

The calculating unit 61 may include a CPU and a memory unit such as a ROM or a RAM, which are not illustrated. The memory unit (not illustrated) of the calculating unit 61 may store a program for inspecting the gloss distribution or the density distribution of the measured object. The program may be executed by the CPU (not illustrated) to provide the various functions of the calculating unit 61. The program may be stored in a computer-readable recording medium, such as an optical computer-readable recording medium or a magnetic computer-readable recording medium. The calculating unit 61 is an example of an image inspecting unit according to the present embodiment.

After the density distribution of one line (one-dimension) is acquired by turning on the density illuminating device 81 and the gloss distribution of one line (one-dimension) is acquired by turning on the gloss illuminating device 51, the image carrying medium 90 is transported by the transporting unit 69 in the X direction of FIG. 9 by a predetermined distance. Then, the density distribution and the gloss distribution of the next one line (one-dimension) are acquired. By repeating this operation, the density distribution and the gloss distribution of the entire (two-dimensional) area of the image carrying medium 90 can be acquired.

The toner image formed by the image forming unit 20 of the image forming apparatus 10 is fused onto the image carrying medium 90, which may include a sheet of paper, by the fusing unit 30, thus producing an output image. The image carrying medium 90 is then fed from the fusing unit 30 onto the image inspecting apparatus 70. In the image inspecting apparatus 70, a density distribution is acquired by the density measuring unit 80 while the image carrying medium 90 is transported by the transporting unit 69, and then the density distribution of the output image on the image carrying medium 90 is inspected by the calculating unit 61. Further, a gloss distribution is acquired by the gloss measuring unit 50, and then the gloss determination of the output image on the image carrying medium 90 is inspected by the calculating unit 61.

Figure 10:
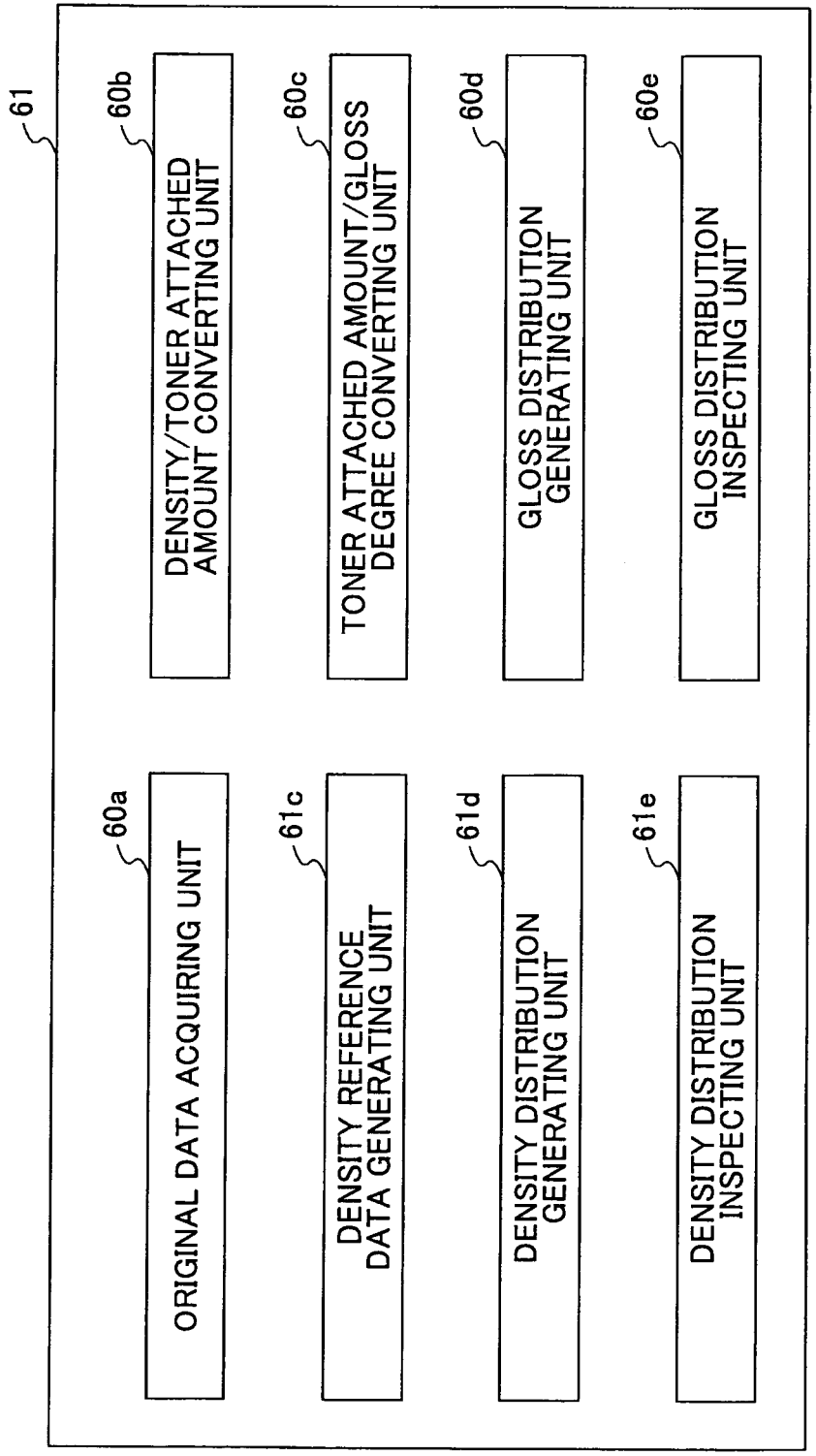
FIG. 10 is a functional block diagram of a calculating unit according to the second embodiment.
Figure 11:
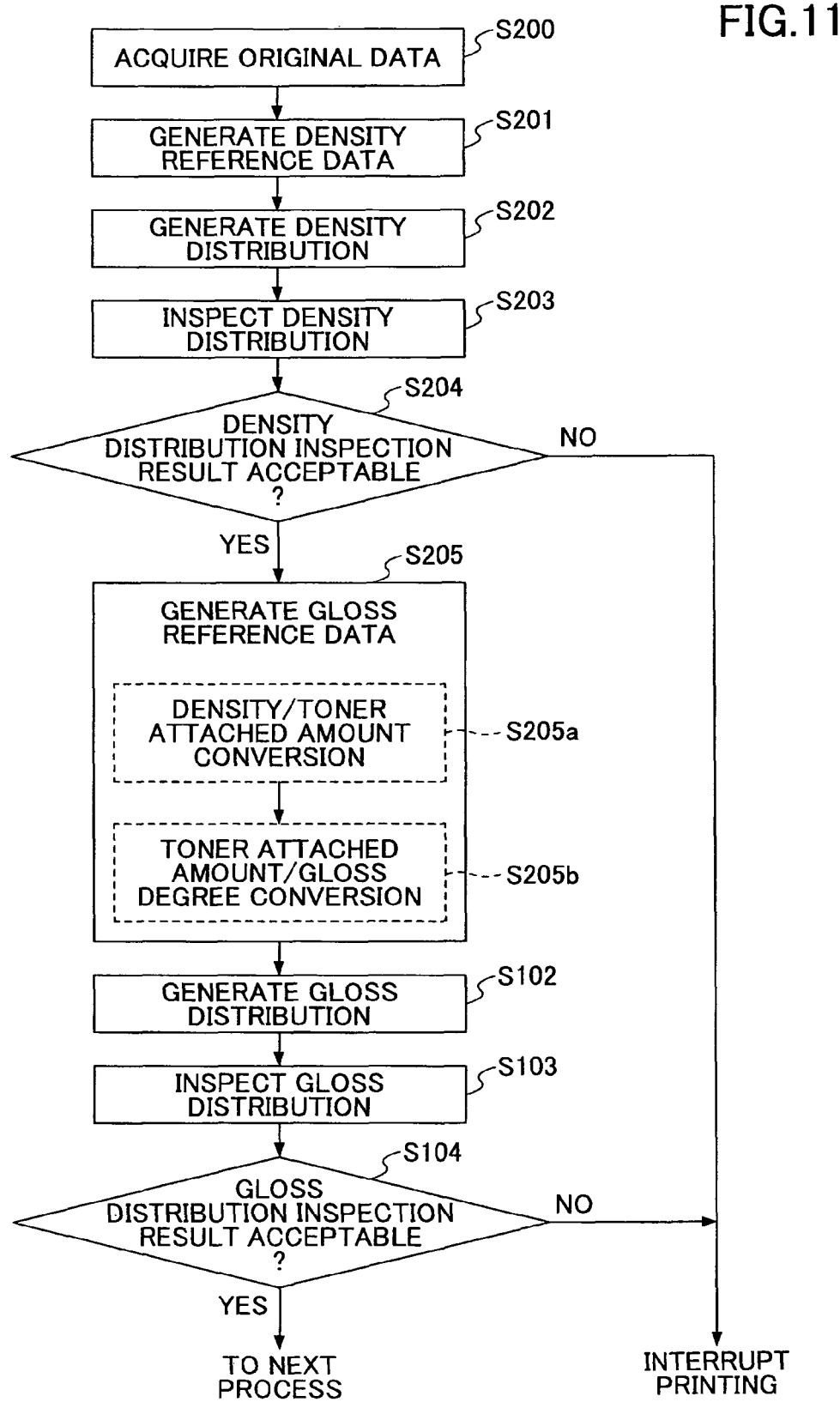
FIG. 11 is a flowchart of a density and gloss distribution inspection process performed by the calculating unit of the second embodiment.

FIG. 10 is a functional block diagram of the calculating unit 61 according to the second embodiment. FIG. 11 is a flowchart of a density and gloss distribution inspection by the calculating unit. With reference to FIGS. 10 and 11, the process is described.

Figure 12:
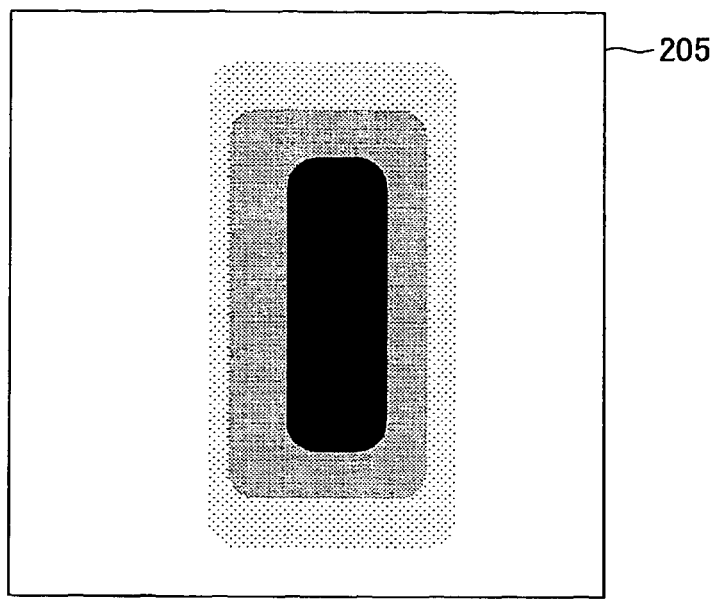
FIG. 12 illustrates density reference data.

In step S200, an original data acquiring unit 60a of the calculating unit 61 acquires density distribution data included in the print data used by the image forming apparatus 10 in forming the output image on the image carrying medium 90. In step S201, a density reference data generating unit 61c of the calculating unit 61 generates density reference data 205 illustrated in FIG. 12 based on the density distribution data included in the print data acquired in step S200.

Figure 13:
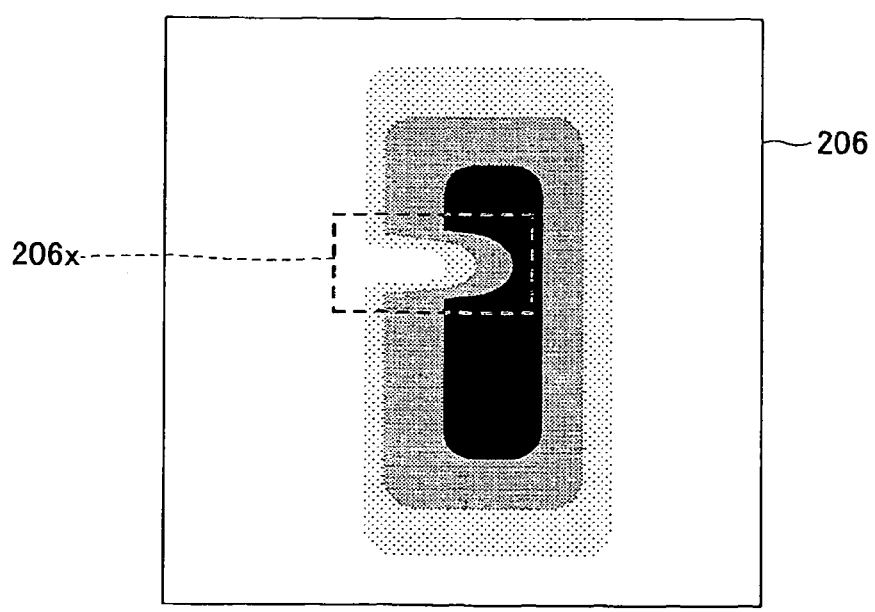
FIG. 13 illustrates a density distribution of an output image formed on an image carrying medium.

In step S202, the density distribution generating unit 61d of the calculating unit 61 generates a density distribution 206 of the output image on the image carrying medium 90 illustrated in FIG. 13, based on the density data of the output image on the image carrying medium 90 that is actually measured by the density measuring unit 80. In other words, the density distribution generating unit 61d generates the density distribution 206 based on the amount of the diffused reflected light received by the imaging device 82 when the density illuminating device 81 is turned on.

The output image on the image carrying medium 90 that is actually measured by the density measuring unit 80 is based on the print data acquired in step S200. In the example of FIG. 13, the density distribution 206 generated by the density distribution generating unit 61d includes an abnormal density portion 206x.

Figure 14:
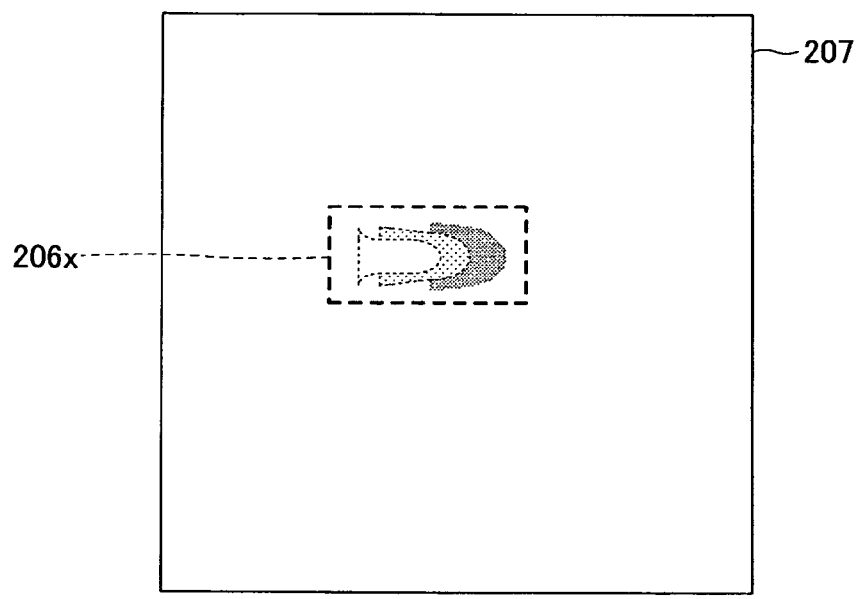
FIG. 14 illustrates a density distribution comparison result.

In step S203, the density distribution inspecting unit 61e of the calculating unit 61 performs density distribution inspection. Specifically, the density distribution inspecting unit 61e compares the density reference data 205 generated in step S201 with the density distribution 206 generated in step S202 on a pixel by pixel basis. Then, the density distribution inspecting unit 61e generates a density distribution comparison result 207 (which includes the abnormal density portion 206x) illustrated in FIG. 14, based on differential data between the density reference data 205 and the density distribution 206 in terms of area or shape, for example.

In step S204, the density distribution inspecting unit 61e of the calculating unit 61 determines whether the result of density distribution inspection in step S203 is acceptable. Specifically, the density distribution inspecting unit 61e determines the acceptability of the density distribution based on whether the density distribution comparison result 207 (including the abnormal density portion 206x) generated in step S203 is within a permissible range.

The acceptability of the density distribution may be determined by comparing the density distribution comparison result 207 (including the abnormal density portion 206x) with comparison data that is stored in the memory unit (not illustrated) of the calculating unit 61 in advance. When it is determined that the density distribution inspection result is acceptable ("YES" in S204), the process moves onto step S205. When the density distribution inspection result is determined to be not acceptable ("NO" in S204), the density distribution inspecting unit 61e determines that there is an image quality problem in terms of density, and interrupts the printing operation (i.e., the forming of an image on the image carrying medium 90) of the image forming apparatus 10. Preferably, step S204 may be omitted when it is not necessary to switch the process depending on whether the result of the density distribution inspection in step S203 is acceptable.

When it is determined in step S204 that the density distribution inspection result is acceptable ("YES" in S204), the density/toner attached amount converting unit 60b and the toner attached amount/gloss degree converting unit 60c of the calculating unit 61 generate gloss reference data in step S205. Specifically, the density/toner attached amount converting unit 60b in step S205a converts the density distribution 206 generated by the density distribution generating unit 61d in step S202 into a toner attached amount on a pixel by pixel basis, as illustrated in FIG. 13, by using a density/toner attached amount conversion chart 200 illustrated in FIG. 4. Thus, the density/toner attached amount converting unit 60b converts not the density distribution data included in the print data acquired in step S200 but the density distribution data (i.e., the density distribution 206 generated by the density distribution generating unit 61d) actually measured by the image inspecting apparatus 70 into a toner attached amount. The density/toner attached amount conversion chart 200 may be designed in accordance with the type of toner used in the image forming apparatus 10. This is because of the fact that the toner attached amount may vary depending on the density of a colorant used in the toner or the toner size may vary even when the density is the same.

Figure 15:
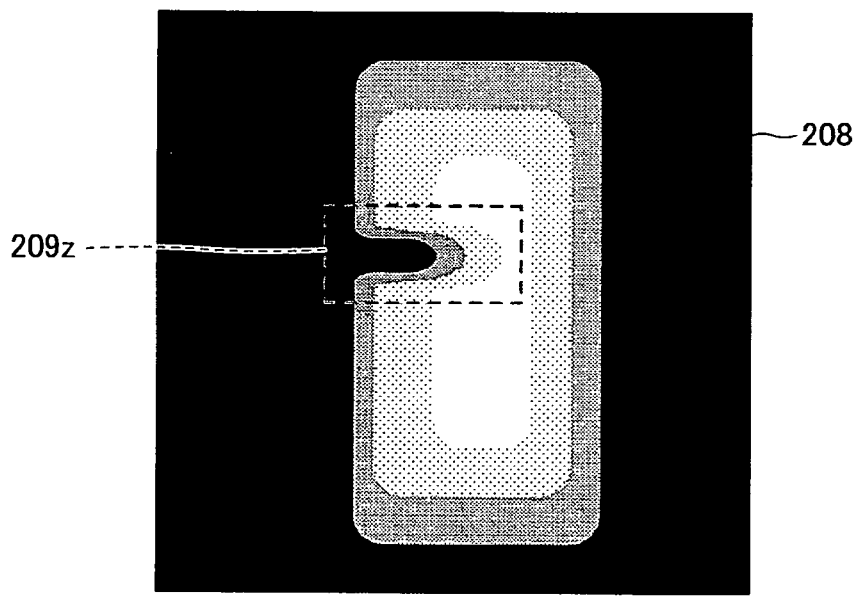
FIG. 15 illustrates a second example of gloss reference data.

In step S205b, the toner attached amount/gloss degree converting unit 60c converts the toner attached amount obtained in step S205a into a gloss degree on a pixel by pixel basis by using the toner attached amount/gloss degree conversion chart 201 illustrated in FIG. 5, thus generating gloss reference data 208 illustrated in FIG. 15 (which includes an abnormal density portion 209z). Thus, in step S205, the toner attached amount/gloss degree converting unit 60c generates the gloss reference data 208 not from the density distribution data included in the print data acquired in step S200 but from the density distribution data actually measured by the image inspecting apparatus 70 (i.e., the density distribution 206 generated by the density distribution generating unit 61d).

The toner attached amount/gloss degree conversion chart 201 may be designed in accordance with the toner used in the image forming apparatus 10 and the characteristics of the fusing unit 30. This is because of the fact that the gloss degree of the image may vary even when the toner attached amount is the same depending on the amount or type of the wax component in the toner used, or the fusing temperature.

Figure 16:
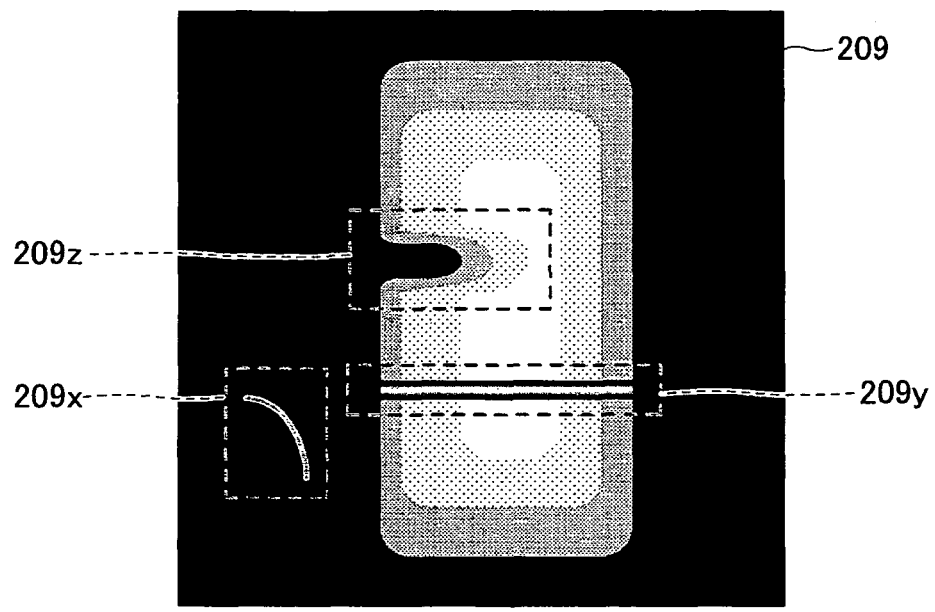
FIG. 16 illustrates a second example of a gloss distribution of an output image formed on the image carrying medium.

In step S102, the gloss distribution generating unit 60d of the calculating unit 61 generates a gloss distribution 209 of the output image on the image carrying medium 90, as illustrated in FIG. 16, based on the gloss data of the output image on the image carrying medium 90 that is actually measured by the gloss measuring unit 50. The output image on the image carrying medium 90 that is actually measured by the gloss measuring unit 50 is based on the print data acquired in step S200. In the example of FIG. 16, the gloss distribution 209 generated by the gloss distribution generating unit 60d includes abnormal gloss portions 209x and 209y and an abnormal density portion 209z.

Then, in step S103, the gloss distribution inspection unit 60e of the calculating unit 61 performs gloss distribution inspection. Specifically, the gloss distribution inspection unit 60e compares the gloss reference data 208 generated in step S205 with the gloss distribution 209 generated in step S102 on a pixel by pixel basis. Then, based on differential data between the gloss reference data 208 and the gloss distribution 209 in order to area and shape, for example, the gloss distribution inspection unit 60e generates the gloss distribution comparison result 210 (including the abnormal gloss portions 209x and 209y) illustrated in FIG. 17. The gloss distribution comparison result 210 does not include the abnormal density portion 209z.

Then, in step S104, the gloss distribution inspection unit 60e of the calculating unit 61 determines whether the result of the gloss distribution inspection performed in step S103 is acceptable. Specifically, the gloss distribution inspection unit 60e determines the acceptability of the gloss distribution based on whether the gloss distribution comparison result 210 (including the abnormal gloss portions 209x and 209y) detected in step S103 is within a permissible range.

The determination of the acceptability of the gloss distribution may involve comparing the gloss distribution comparison result 210 (including the abnormal gloss portions 209x and 209y) with comparison data that is stored in a memory unit (not illustrated) of the calculating unit 61 in advance. When the gloss distribution inspection result is determined to be acceptable ("YES" in S104), the process advances to the next step. When the gloss distribution inspection result is determined to be not acceptable ("NO" in S104), the gloss distribution inspection unit 60e determines that there is an image quality problem in terms of gloss, and interrupts the printing operation (i.e., the forming of an image on the image carrying medium 90) of the image forming apparatus 10. Preferably, step S104 may be omitted when it is not necessary to switch the process depending on the result of the gloss distribution inspection in S103.

As described above, in step S205a, the density/toner attached amount converting unit 60b converts the density distribution 206 of FIG. 13 generated by the density distribution generating unit 61d in step S202 into the toner attached amount on a pixel by pixel basis. In step S205b, the toner attached amount/gloss degree converting unit 60c converts the toner attached amount obtained in step S205a into the gloss degree on a pixel by pixel basis, thus generating the gloss reference data 208 illustrated in FIG. 15.

Figure 18:
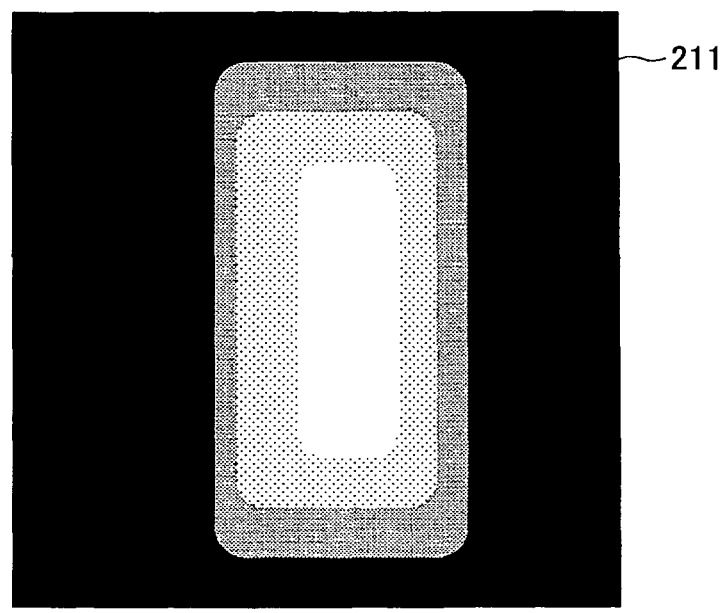
FIG. 18 illustrates a third example of gloss reference data.

If the gloss reference data is generated not from the density distribution 206 (see FIG. 13) generated in steps S205a and S205b which is based on the density data actually measured by the density measuring unit 80 but from the density reference data 205 (see FIG. 12) generated based on the density distribution data included in the print data, gloss reference data 211 illustrated in FIG. 18 is generated instead of the gloss reference data 208 illustrated in FIG. 15.

Figure 17:
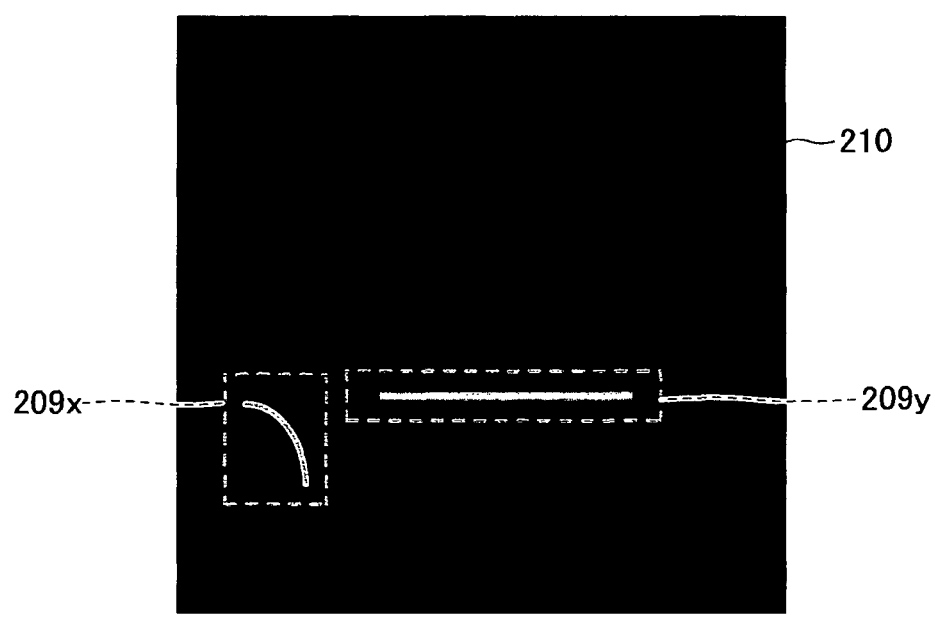
FIG. 17 illustrates a second example of a gloss distribution comparison result.
Figure 19:
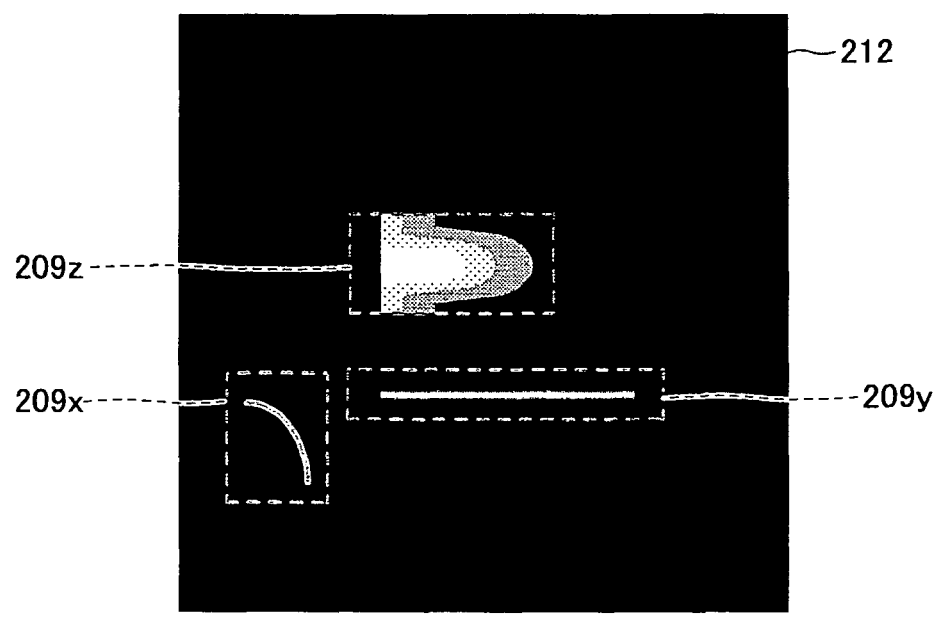
FIG. 19 illustrates a third example of a gloss distribution comparison result.

In this case, when the gloss distribution inspection unit 60e compares in step S103 the gloss reference data 211 with the gloss distribution 209 generated in step S102 on a pixel by pixel basis, the gloss distribution comparison result 212 illustrated in FIG. 19 is generated, instead of the gloss distribution comparison result 210 illustrated in FIG. 17. In the case of FIG. 19, the gloss distribution comparison result 212 includes not only the abnormal gloss portions 209x and 209y but also the abnormal density portion 209z. Namely, abnormality determination cannot be made in terms of gloss alone.

Thus, during the image inspection of the output image on the image carrying medium 90 by the calculating unit 61, the acceptability of density distribution and gloss distribution can be determined. Namely, density abnormality determination and gloss abnormality determination can be performed. Preferably, the density/toner attached amount conversion chart 200 and the toner attached amount/gloss degree conversion chart 201 used during the image inspection by the calculating unit 61 may be combined into a single density/gloss degree conversion chart. This feature is particularly effective when there is no need to switch the process depending on the toner attached amount, or when the capacity of the memory unit (not illustrated) of the calculating unit 61 is small.

Thus, in accordance with the second embodiment, the gloss reference data is generated from the density distribution data actually measured by the image inspecting apparatus, by using the density/toner attached amount conversion chart and the toner attached amount/gloss degree conversion chart. As a result, in addition to the effects provided by the first embodiment, the following effect can be obtained. Specifically, even when there is a density distribution defect, a portion that is defective only in terms of gloss and which has a normal density can be identified without determining the density distribution defect to be a gloss abnormality. If the gloss reference data is generated not from the density distribution data actually measured by the image inspecting apparatus but from the density reference data generated based on the density distribution data included in the print data, an abnormal density portion would also be detected during the gloss abnormality inspection, thus preventing the abnormality determination in terms of gloss alone.

<Variation 1>

In accordance with variation 1, which is a variation of the first embodiment, the image forming apparatus 10 forms a full-color image including plural image-forming colors, and the full-color image is inspected by the image inspecting apparatus. The image forming apparatus 10 of variation 1 includes a calculating unit 62 instead of the calculating unit 60 of the image forming apparatus 10. The image forming apparatus 10 forms the full-color image by superposing images of the four image-forming colors of cyan, magenta, yellow, and black. The gray levels of an image, particularly a natural image, are formed by the superposition of halftone dot images of toner of the various colors of cyan, magenta, and yellow, with each of the image-forming colors having a density distribution.

The calculating unit 62 inspects the output image formed on the image carrying medium 90 based on the image data (i.e., the print data used by the image forming apparatus 10 in forming the output image on the image carrying medium 90) acquired from the image forming apparatus 10 and the gloss distribution of the output image on the image carrying medium 90 that is actually measured by the gloss measuring unit 50.

The calculating unit 62 may include a CPU and a memory unit, such as a ROM and a RAM, which are not illustrated. The memory unit (not illustrated) of the calculating unit 62 may store a program for inspecting gloss distribution. The program may be executed by the CPU (not illustrated) to provide the various functions of the calculating unit 62. The program may be recorded in a computer-readable recording medium such as an optical computer-readable recording medium or a magnetic computer-readable recording medium. The calculating unit 62 is an example of an image inspecting unit according to the present embodiment.

Figure 20:
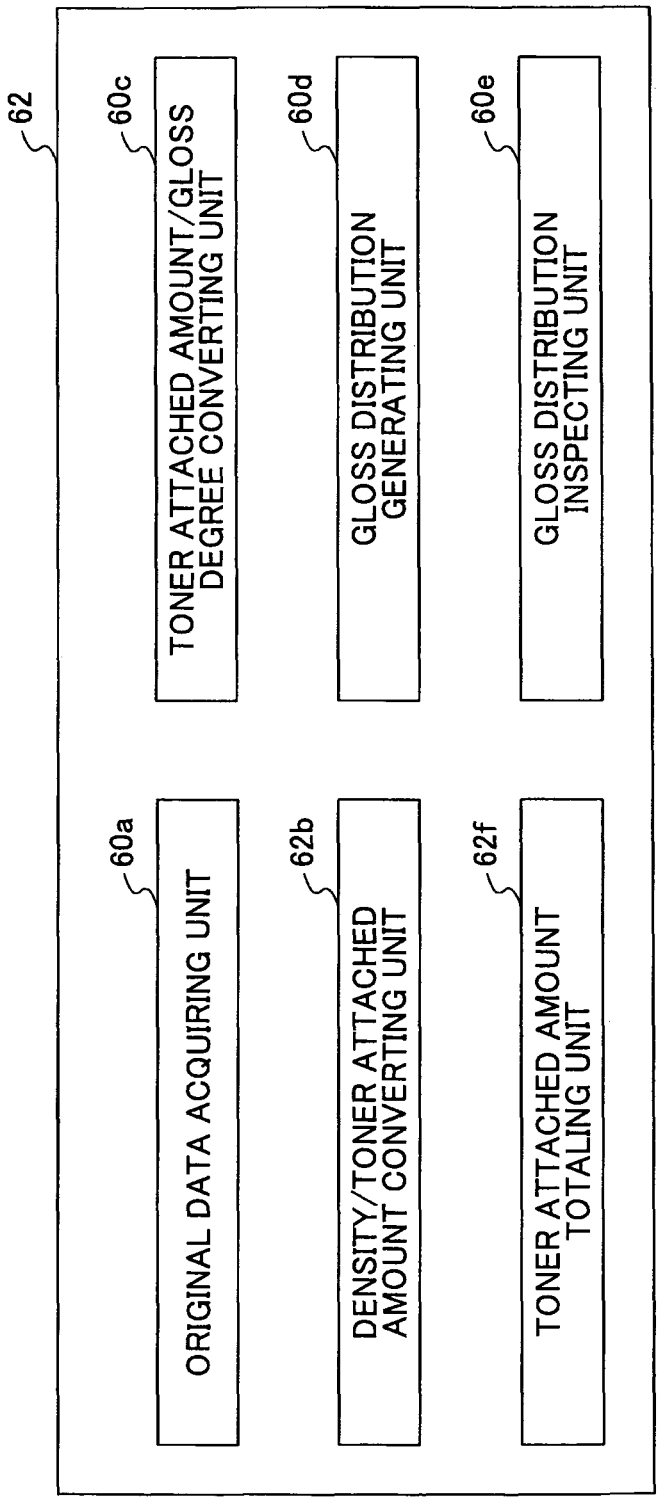
FIG. 20 is a functional block diagram of a calculating unit according to variation 1.
Figure 21:
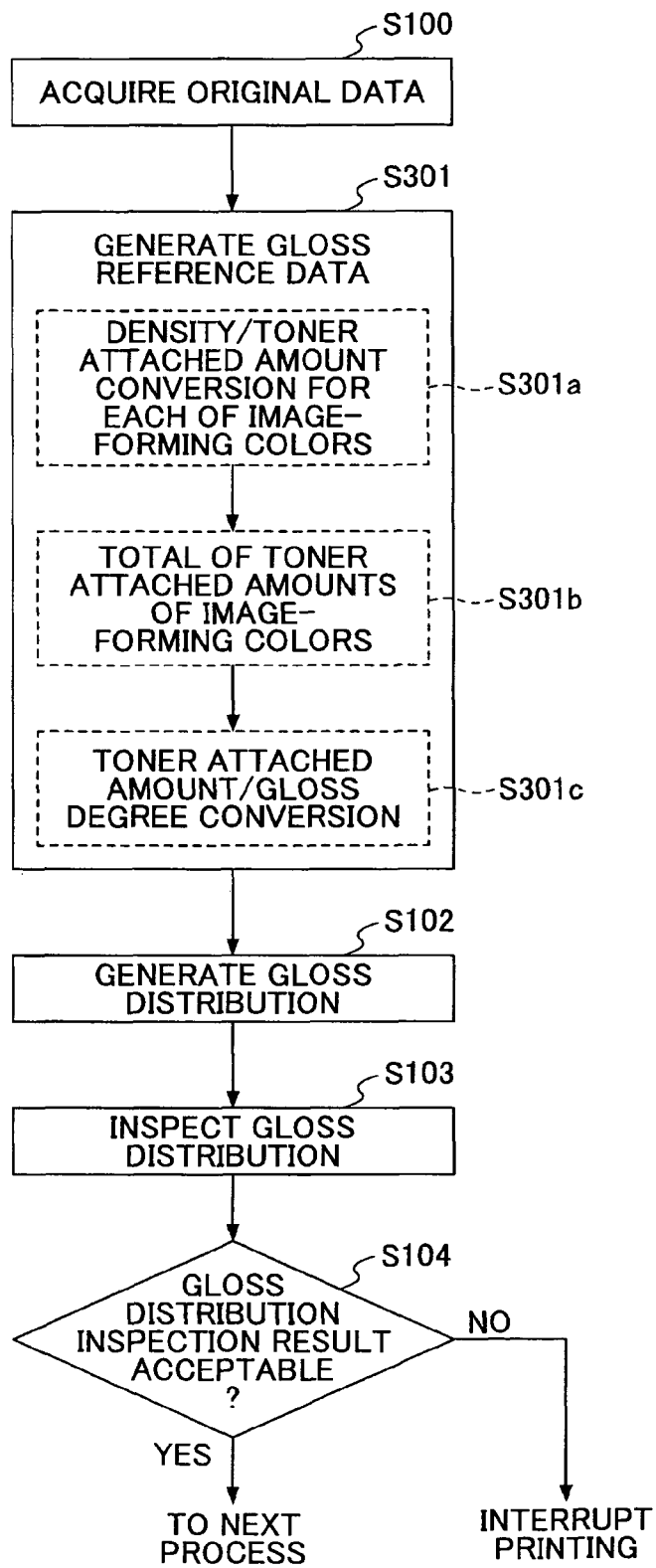
FIG. 21 is a flowchart of a gloss distribution inspection process performed by a calculating unit according to variation 1.

FIG. 20 is a functional block diagram of the calculating unit 62 according to variation 1. FIG. 21 is a flowchart of a gloss distribution inspection process performed by the calculating unit 62. The gloss distribution inspection process is described with reference to FIGS. 20 and 21.

In step S100, the original data acquiring unit 60a of the calculating unit 62 acquires the print data used by the image forming apparatus 10 in forming the output image on the image carrying medium 90. The print data is acquired for each of the image-forming colors of cyan, magenta, yellow, and black.

In step S301, a density/toner attached amount converting unit 62b, a toner attached amount totaling unit 62f, and a toner attached amount/gloss degree converting unit 60c of the calculating unit 62 generate gloss reference data. Specifically, in step S301a, the density/toner attached amount converting unit 62b, by using the density/toner attached amount conversion chart 200 illustrated in FIG. 4, converts the density distribution data included in the print data acquired in step S100 for each of the image-forming colors into a toner attached amount on a pixel by pixel basis. The density/toner attached amount conversion chart 200 may be designed in accordance with the type of the toner used in the image forming apparatus 10. This is due to the fact that the toner attached amount may vary even when the density is the same depending on the density of colorant used in the toner or the toner size.

In step S301b, the toner attached amount totaling unit 62f calculates a total of the toner attached amounts of the image-forming colors on a pixel by pixel basis. The total of the toner attached amounts of the image-forming colors is calculated on a pixel by pixel basis because the gloss distribution generally varies depending on the toner attached amount regardless of the image-forming color. Namely, the total value of the attached amounts of the toners of the various image-forming colors is more important than the toner attached amount of a single color.

In step S301c, the toner attached amount/gloss degree converting unit 60c, by using the toner attached amount/gloss degree conversion chart 201 of FIG. 5, generates gloss reference data 202 illustrated in FIG. 6 by converting the total toner attached amount calculated in step S301b into a gloss degree. Namely, the toner attached amount/gloss degree converting unit 60c generates the gloss reference data 202 by converting the total toner attached amount calculated by the toner attached amount totaling unit 62f into the gloss degree on a pixel by pixel basis. The toner attached amount/gloss degree conversion chart 201 may be designed in accordance with the toner used in the image forming apparatus and the characteristics of the fusing unit. This is due to the fact that the gloss degree of an image may vary even when the toner attached amount is the same, depending on the amount or type of a wax component in the toner used or the fusing temperature.

Then, steps S102 through S104 are performed as described above, whereby, during the image inspection of the full-color output image formed on the image carrying medium 90 by the image forming apparatus, the acceptability of the gloss distribution may be determined (gloss abnormality determination). Preferably, the density/toner attached amount conversion chart 200 and the toner attached amount/gloss degree conversion chart 201 used in the image inspection by the calculating unit 62 may be combined into a single density/gloss degree conversion chart. This feature is particularly effective when there is no need for switching the process depending on the toner attached amount, or when the capacity of the memory unit (not illustrated) of the calculating unit 62 is small. Preferably, step S104 may be omitted when it is not necessary to switch the process depending on the result of gloss distribution inspection in step S103.

Thus, in accordance with variation 1, when a full-color image is inspected by the image inspecting apparatus, the gloss reference data is calculated by totaling the toner attached amounts of the image-forming colors of cyan, magenta, and yellow in view of the fact that the gloss of a mixed color portion is different from the gloss of each individual toner at its own density. Thus, in addition to the effects of the first embodiment, the following effect can be provided. Namely, even when the color image has gray levels, such as in the case of a natural image, a portion having a gloss defect can be accurately detected.

<Variation 2>

In accordance with variation 2, which is a variation of the second embodiment, the image forming apparatus forms a full-color image (including plural image-forming colors), and the image inspecting apparatus inspects the full-color image. The image forming apparatus according to variation 2 includes a calculating unit 63 instead of the calculating unit 61 of the image forming apparatus 10. In accordance with variation 2, the image forming apparatus forms the full-color image by superposing the images of the four image-forming colors of cyan, magenta, yellow, and black. When the gray levels of an image, particularly a natural image, are formed by superposition of the halftone dot images of the four toner colors of cyan, magenta, and yellow, each of the image-forming colors has a density distribution.

The calculating unit 63 inspects the output image formed on the image carrying medium 90 based on the image data (i.e., the print data used by the image forming apparatus 10 in forming the output image on the image carrying medium 90) acquired from the image forming apparatus 10 and the gloss distribution of the output image on the image carrying medium 90 that is actually measured by the gloss measuring unit 50.

The calculating unit 63 may include a CPU and a memory unit, such as a ROM and a RAM, which are not illustrated. The memory unit (not illustrated) of the calculating unit 63 may record a program for inspecting a gloss distribution or a density distribution. The program may be executed by the CPU (not illustrated) to provide the various functions of the calculating unit 63. Preferably, the program may be stored in a computer-readable recording medium, such as an optical computer-readable recording medium or a magnetic computer-readable recording medium. The calculating unit 63 is an example of an image inspecting unit according to the present embodiment.

Figure 22:
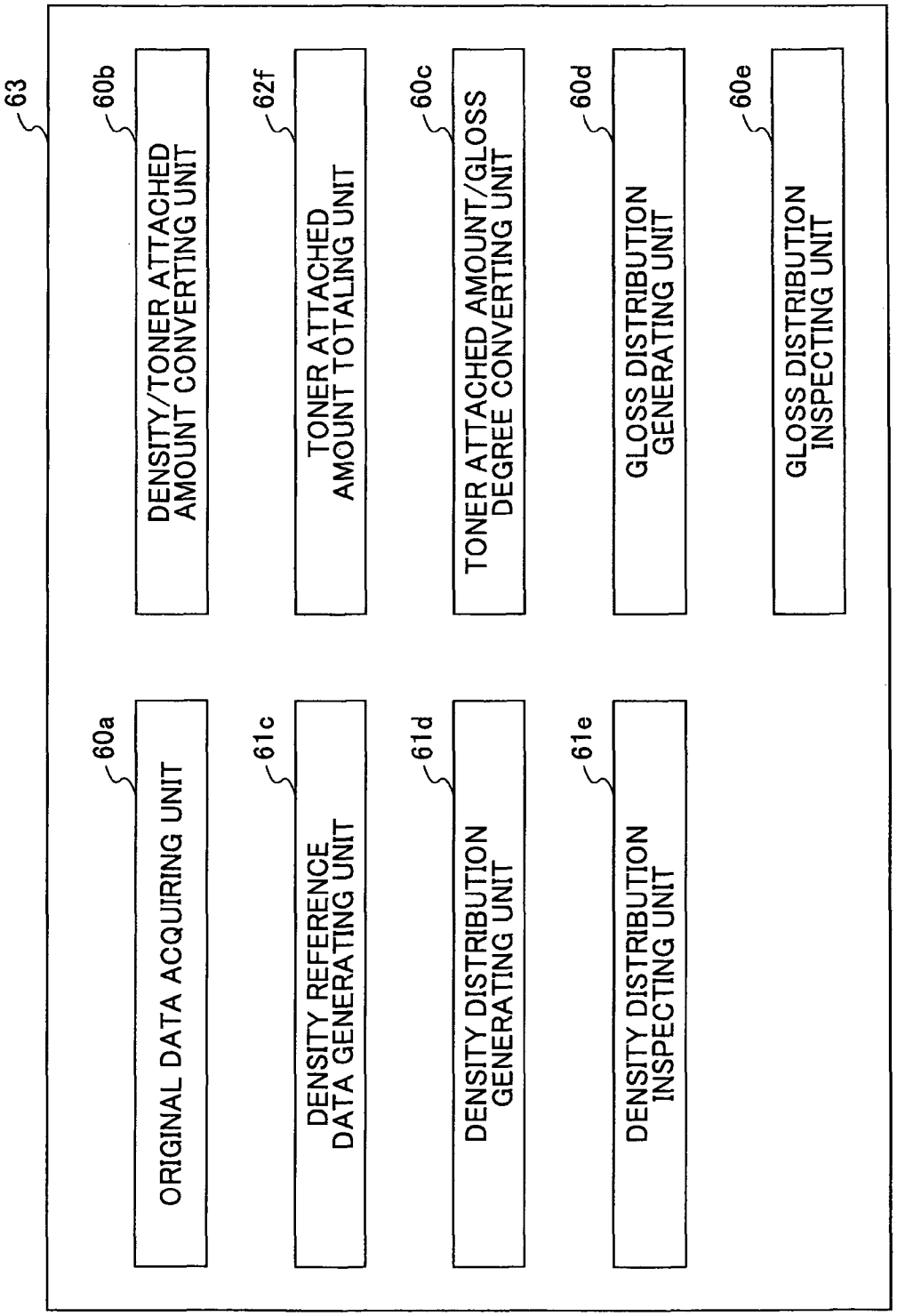
FIG. 22 is a functional block diagram of the calculating unit according to variation 2.
Figure 23:
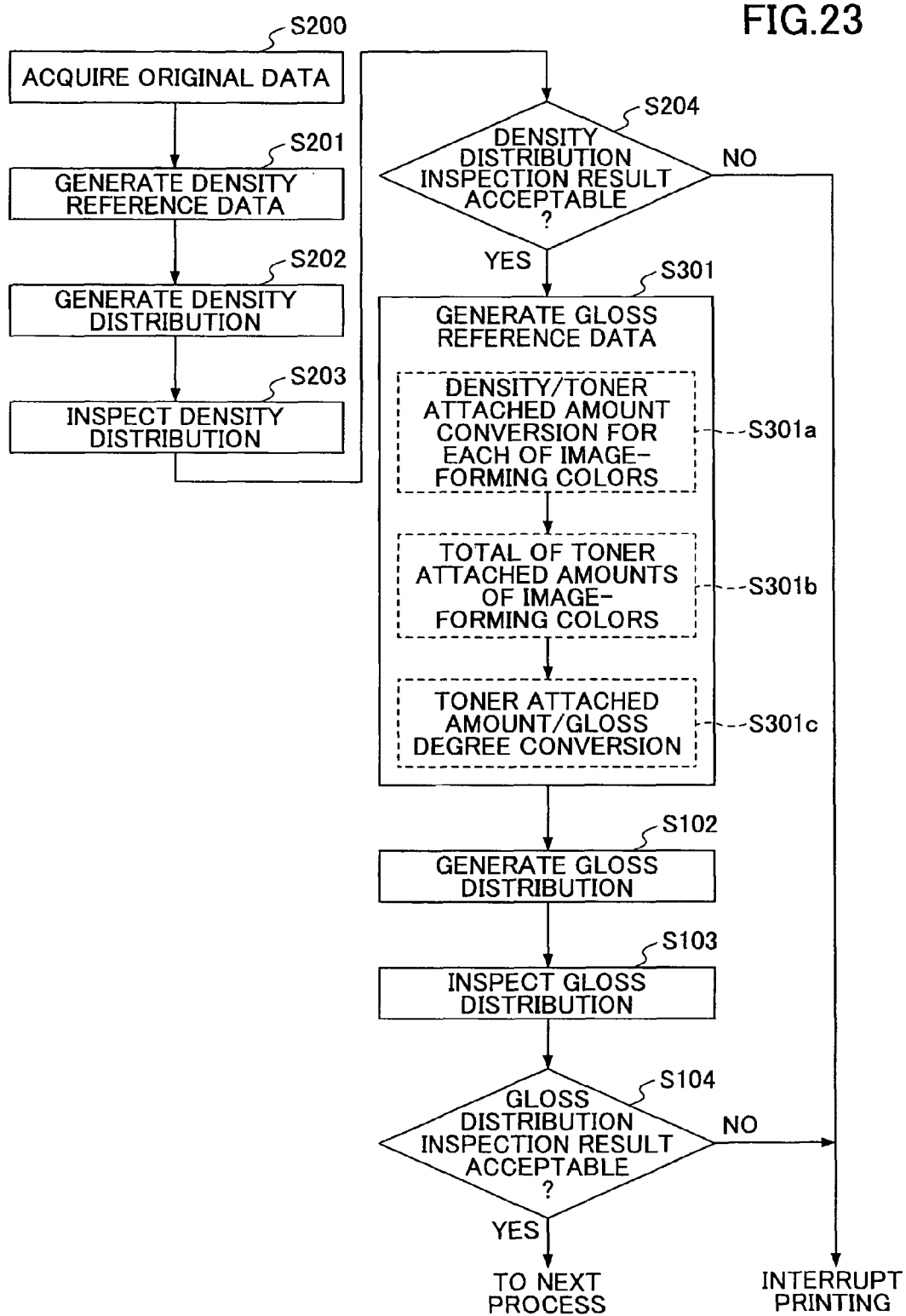
FIG. 23 is a flowchart of a density and gloss distribution inspection process performed by the calculating unit according to variation 2.

FIG. 22 is a functional block diagram of the calculating unit 63 according to variation 2. FIG. 23 is a flowchart of a density and gloss distribution inspection process performed by the calculating unit according to variation 2.

First, a process similar to the process of steps S200 through S204 of FIG. 11 is performed to inspect a density distribution. Preferably, step S204 may be omitted when it is not necessary to switch the process depending on the result of the density distribution inspection performed in step S203.

Then, a process similar to the process of steps S301 and steps S102 through S104 of FIG. 21 are performed to inspect a gloss distribution. In this way, as in the case of variation 1, image inspection can be performed on the full-color image. However, in step S301, the gloss reference data is generated not from the density reference data based on the density distribution data included in the print data, but from the density distribution data actually measured by the image inspecting apparatus. As a result, the same effects as those of the second embodiment can be obtained. Preferably, step S104 may be omitted when it is not necessary to switch the process depending on the result of the gloss distribution inspection performed in step S103.

Thus, in accordance with variation 2, when the image inspecting apparatus inspects a full-color image, the toner attached amount is determined for each of the image-forming colors because the gloss of a mixed portion of the various colors of cyan, magenta, and yellow may be different from the gloss of each individual toner with its own density. Thereafter, a total of the toner attached amounts of the image-forming colors is calculated to obtain the gloss reference data. As a result, in addition to the effects similar to those of the second embodiment, the following effect can be obtained. Namely, even when the color image has gray levels, such as in the case of a natural image, a portion having a gloss defect can be accurately identified.

<Variation 3>

In accordance with variation 3, which is a variation of the first and the second embodiments, plural toner attached amount/gloss degree conversion charts are prepared, of which one is selected depending on the fusing control condition and the like.

In electrophotographic image forming apparatuses, particularly those adapted for digital printing, in order to address the demand for high image quality, a gloss control process involving the fusing temperature control may be performed. Also, sheets with various types of gloss, such as "gloss paper" and "semi-gloss paper" are available, in addition to the prior-art sheets which may be referred to as "normal paper". While the gloss value of an image may vary upon fusing, the gloss value may also be greatly influenced by the condition of the sheet as the base, as well as by the fusing condition. This means that the gloss distribution may vary depending on the fusing control condition or the type of sheet even when the density distribution is the same.

Figure 24:
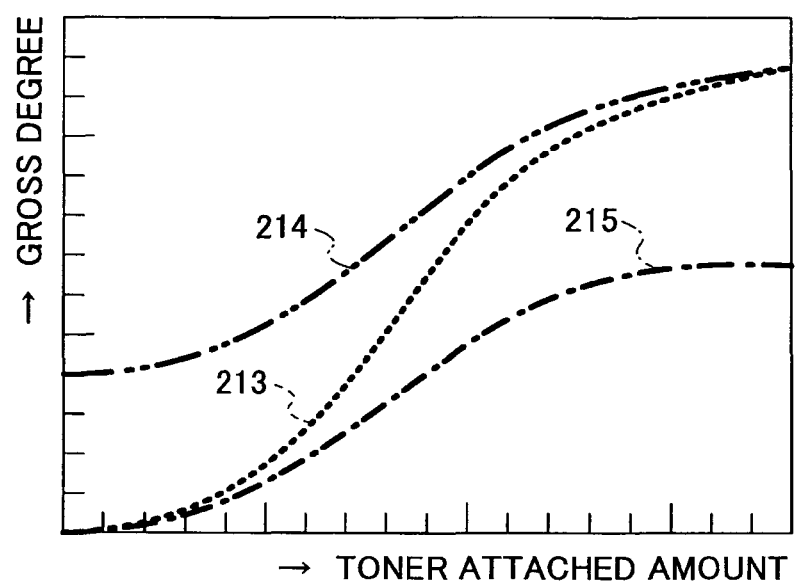
FIG. 24 is a second example of a toner attached amount/gloss degree conversion chart.

Thus, in accordance with variation 3, the toner attached amount/gloss degree conversion chart is changed depending on the fusing control condition or the type of the image carrying medium. FIG. 24 is an example of the toner attached amount/gloss degree conversion chart. For example, when an image is fused on a normal paper at a normal temperature, the gloss degree can be accurately predicted from the toner attached amount based on the table value 213 illustrated in FIG. 24.

However, when the image is to be fused on a gloss paper at the normal temperature, because the sheet is glossy even before the toner is attached onto it, the gloss degree of the image cannot be accurately predicted from the table values 213. In this case, the gloss degree can be accurately predicted from the toner attached amount based on the table values 214.

When fusing is performed by using a normal paper and at a low temperature, because the smoothness of the resultant toner surface is not high, the gloss degree cannot be increased much even by increasing the toner attached amount. Thus, the gloss degree cannot be accurately predicted by using the table values 213. Thus, in such a case, the gloss degree can be accurately predicted from the toner attached amount by using the table values 215.

Thus, in accordance with variation 3, the toner attached amount/gloss degree converting unit 60c generates the gloss reference data by selecting one of the plural toner attached amount/gloss degree conversion charts depending on the fusing control condition or the type of the image carrying medium on which the image is to be formed. In this way, the gloss degree can be accurately predicted from the toner attached amount.

For example, the conversion charts are prepared in advance for various types of image carrying media and fusing temperatures. Such conversion charts may include those where fusing is performed on normal paper at a normal temperature, a low temperature, and a high temperature, and those where fusing is performed on a gloss paper at the normal temperature, the low temperature, and the high temperature. The types of the image carrying media may include semi-gloss paper as well as the normal paper and the gloss paper. By appropriately selecting the conversion chart in the process of converting the toner attached amount into a gloss degree, the gloss degree can be accurately predicted from the toner attached amount.

<Variation 4>

In accordance with variation 4, which is a variation of the first and the second embodiments, one of plural toner attached amount/gloss degree conversion charts is selected depending on an image area.

In electrophotographic image forming apparatuses, particularly those adapted for digital printing, a gloss control process involving fusing temperature control may be performed in order to address the need for high image quality. For example, the fusing temperature may be varied depending on the image content (i.e., a specific image area). For example, the background of an image may have a low gloss while its content (i.e., a specific image area) may have a high gloss. In this case, the image forming apparatus may be fed with information indicating which image area has a low gloss and which image area has a high gloss, together with the print data. For example, each of the pixels may be associated with numerical information indicating low gloss or high gloss.

Thus, in accordance with variation 4, the toner attached amount/gloss degree conversion chart is changed depending on the image area. With reference to FIG. 24, a high gloss may be obtained in the content image area that is fused at a high temperature when the toner attached amount is small. As a result, the gloss degree cannot be accurately predicted from the table values 213. Thus, in such a case, the gloss degree can be accurately predicted from the toner attached amount by using the table values 214.

On the other hand, in the background area that is fused at a low temperature, the gloss degree cannot be increased much even when the toner attached amount is increased because the smoothness of the resultant toner surface is not high. As a result, the gloss degree cannot be accurately predicted when the table values 213 are used. In such a case, the gloss degree can be accurately predicted from the toner attached amount by using the table values 215.

Thus, in accordance with variation 4, the toner attached amount/gloss degree converting unit 60c generates the gloss reference data by selecting one of the plural toner attached amount/gloss degree conversion charts depending on the image area of the print data. In this way, the gloss degree can be accurately predicted from the toner attached amount.

For example, the conversion charts are prepared for the case where the background area is fused at a low temperature and the case where the specific content is fused at a high temperature. Then, in the process of converting the toner attached amount into the gloss degree, the gloss degree can be accurately predicted from the toner attached amount by selecting an appropriate conversion chart.

<Variation 5>

In accordance with variation 5, which is a variation of the first and the second embodiments, an image area to which no toner is attached is identified upon calculation of the toner attached amount distribution from the density distribution data, and then the image area with no toner is inspected for a gloss defect in a different manner from an image area with toner. The image forming apparatus according to variation 5 includes a calculating unit 64 instead of the calculating unit 61 of the image forming apparatus 10. While the following description is made with reference to the second embodiment, the process according to variation 5 is similarly applicable to the first embodiment because the process is performed after the toner attached amount has been determined.

The calculating unit 64 inspects the output image on the image carrying medium 90 based on the image data (i.e., the print data used by the image forming apparatus 10 in forming the output image on the image carrying medium 90) acquired from the image forming apparatus 10 and the gloss distribution of the output image on the image carrying medium 90 that is actually measured by the gloss measuring unit 50.

The calculating unit 64 may include a CPU and a memory unit, such as a ROM or a RAM, which are not illustrated. The memory unit (not illustrated) of the calculating unit 64 may store a program for inspecting a gloss distribution or a density distribution. The program may be executed by the CPU (not illustrated) to provide the various functions of the calculating unit 64. The program may be stored in a computer-readable recording medium, such as an optical computer-readable recording medium or a magnetic computer-readable recording medium. The calculating unit 64 is an example of the image inspecting unit according to the present embodiment.

Figure 25:
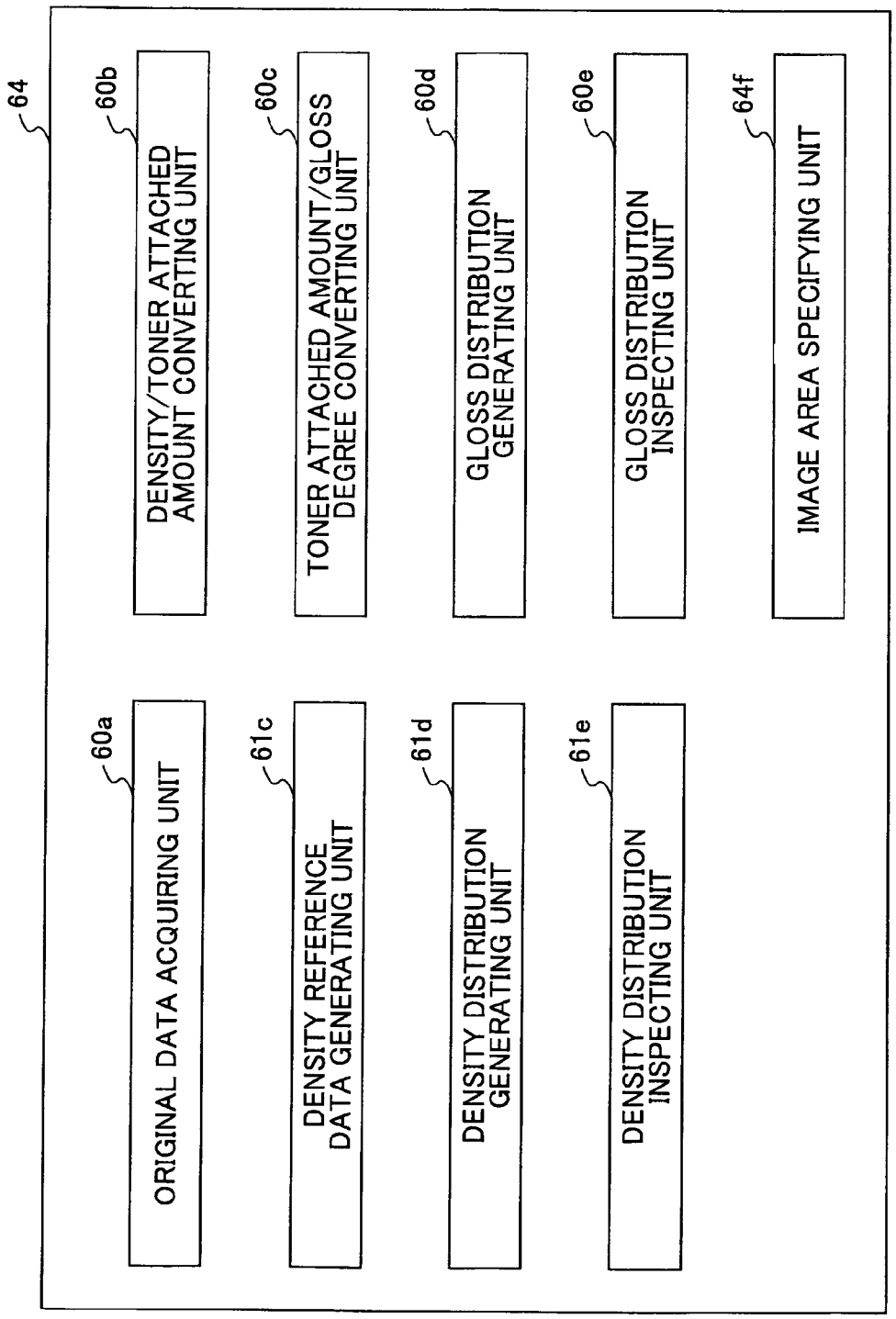
FIG. 25 is a functional block diagram of a calculating unit according to variation 5.
Figure 26:
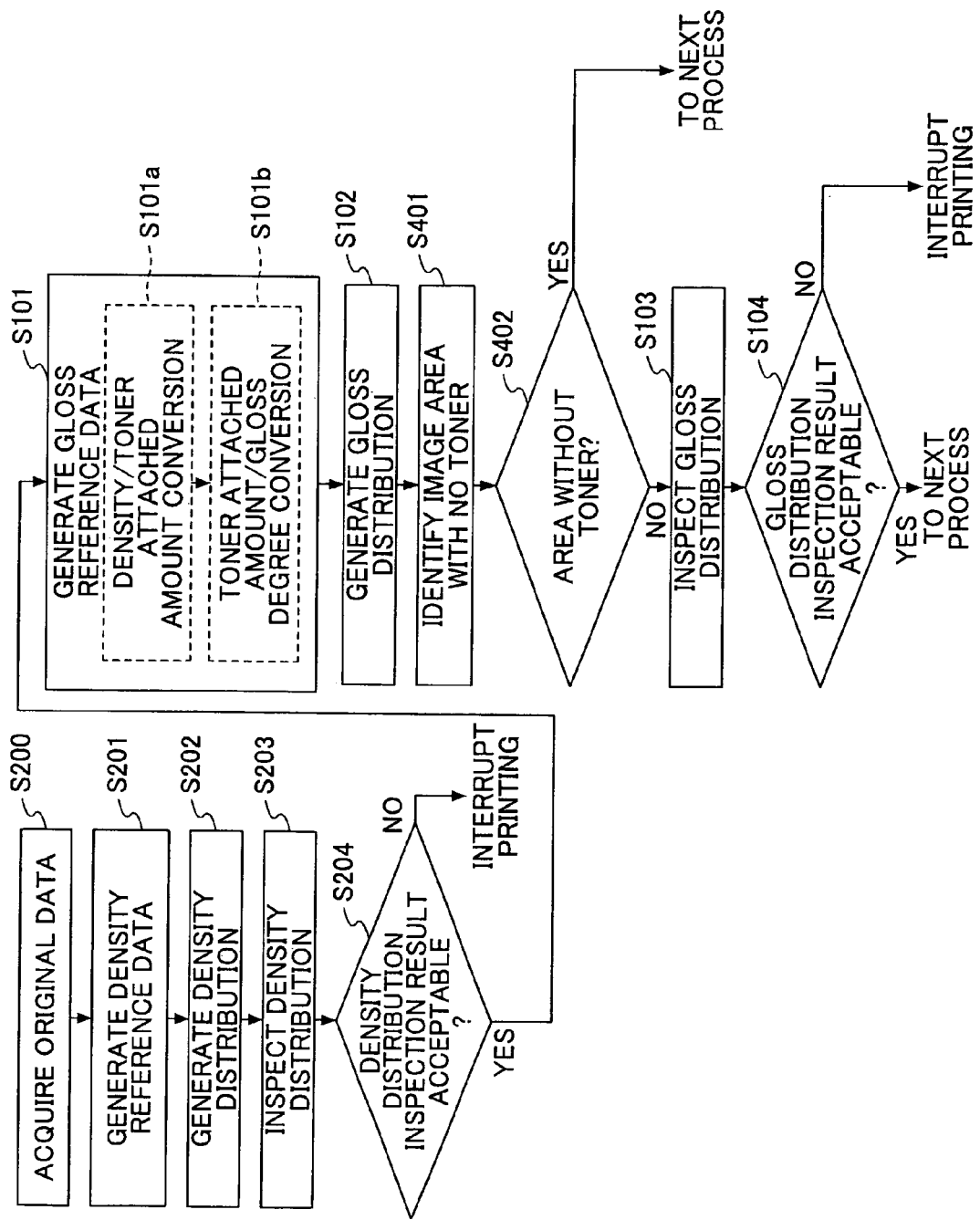
FIG. 26 is a flowchart of a density and gloss distribution inspection process performed by the calculating unit of variation 5.

FIG. 25 is a functional block diagram of the calculating unit 64 according to variation 5. FIG. 26 is a flowchart of a density and gloss distribution inspection process performed by the calculating unit of variation 5. With reference to FIGS. 25 and 26, the process performed by the calculating unit 64 is described.

First, a process similar to the process of steps S200 through S204 of FIG. 11 is performed in order to inspect a density distribution. Preferably, step S204 may be omitted when it is not necessary to switch the process depending on the result of the density distribution inspection performed in step S203.

Then, a process similar to the process of steps S101 and S102 of FIG. 11 is performed. In step S101, the gloss reference data may be generated from the density reference data generated based on the density distribution data included in the print data. Preferably, the gloss reference data may be generated from the density distribution data actually measured by the image inspecting apparatus, so that the same effects as those of the second embodiment can be obtained.

Then, in step S401, the image area specifying unit 64*f*, based on, the toner attached amount generated by the density/toner attached amount converting unit 60*b* in step S101, identifies an image area where no toner is attached in order to determine the acceptability of a gloss defect in a different manner from the case of determining the acceptability of an area with toner. "Different manner" may refer to the changing of the determination standard (such as changing a threshold value or a determination method), or not making the gloss defect determination at all in the image area with no toner. In the following description of variation 5, no gloss defect determination is made for the image area with no toner.

When the density distribution data is converted into the toner attached amount in step S101, an image area to which toner is attached is recognized (because the image area has high gloss due to the toner), so that an image area with no toner can be easily identified. Preferably, the image area with no toner may be identified from the density distribution data included in the print data.

Then, in step S402, it is determined whether an area for gloss distribution inspection corresponds to the image area with no toner identified in step S401. When it is determined that the inspected area corresponds to the image area with no toner identified in step S401 ("YES" in S402), the process advances to the next step without performing the gloss distribution inspection. When it is determined that the area does not correspond to the image area with no toner identified in step S401 ("NO" in S402), a process similar to steps S103 and S104 of FIG. 11 is performed. Thus, the gloss distribution inspection process can be performed only for the image area with toner. Preferably, step S104 may be omitted when it is not necessary to switch the process depending on the result of the gloss distribution inspection performed in step S103.

Thus, in accordance with variation 5, an image area with no toner is identified upon calculation of the toner attached amount distribution from the density distribution data, and the gloss defect determination is performed differently from the case of an image area with toner. In this way, the measured object can be appropriately inspected.

For example, an area of a sheet with no toner has the same gloss degree as that of the sheet, which is different from the gloss degree of an area with toner. In this case, a threshold value for gloss defect determination may be switched, or no gloss defect determination may be performed because the gloss of the image area with no toner is the same as the gloss of the sheet.

Figure 27:
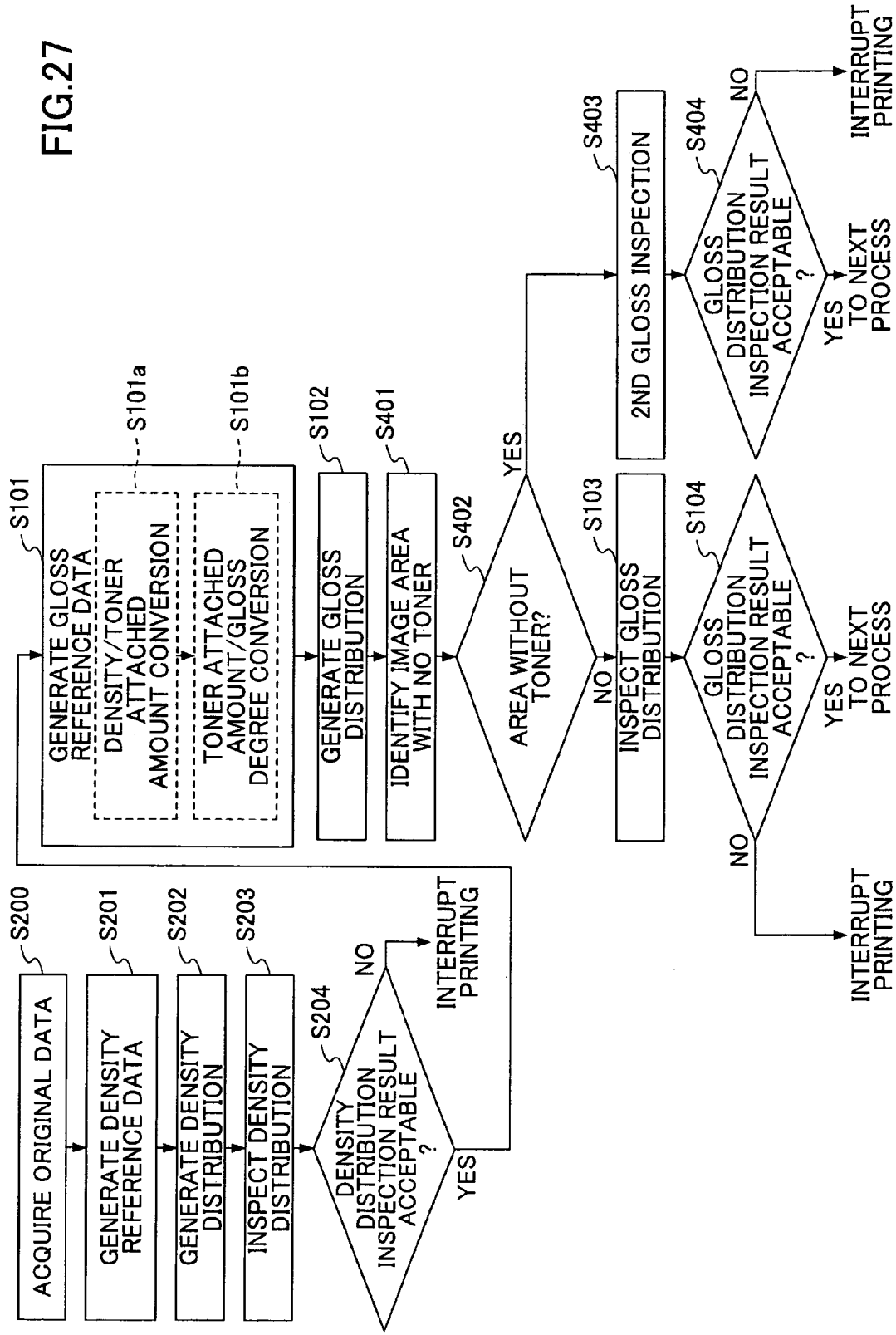
FIG. 27 is a flowchart of another density and gloss distribution inspection process performed by the calculating unit of variation 5.

When it is determined in step S402 of FIG. 26 that the area to be inspected for gloss distribution corresponds to the image area with no toner identified in step S401 ("YES" in S402), steps S403 and S404 of FIG. 27 may be performed. For example, gloss distribution inspection is performed by setting a threshold value for gloss defect determination to a value in step S403 different from that used in step S103. S404 may be similar to S104.

Preferably, step S104 of FIG. 27 may be omitted when it is not necessary to switch the process depending on the result of the gloss distribution inspection performed in step S103. Preferably, step S204 may be omitted when it is not necessary to switch the process depending on the result of the density distribution inspection performed in step S203.

<Variation 6>

In accordance with variation 6, an image inspecting process in a case where the image inspecting apparatus forms a transparent toner image or a white toner image is described.

For example, when the image inspecting apparatus forms a transparent toner image, because the formed toner image does not have any dye, no data corresponding to actually measured density distribution data can be obtained. In this case, the density distribution of the transparent toner image is obtained from the distribution information of the transparent toner in the print data in step S202, for example. The distribution information may include numerical information indicating the intensity of gloss of each pixel in plural levels. With regard to the transparent toner, a density/toner attached amount conversion chart for transparent toner may be used for conversion. The above may apply not only to the transparent toner but also to white toner. When the white toner is used as a base coat, an increased gloss degree may be obtained.

Thus, the density/toner attached amount converting unit 60*b*, based on the distribution information of at least one of the transparent toner image and the white toner image included in the print data, converts the density distribution data of at least one of the transparent toner image and the white toner image into a toner attached amount.

Thus, in accordance with variation 6, in the case of a transparent toner image having no dye, the distribution information of the transparent toner included in the print data is utilized because no data corresponding to the actually measured density distribution data can be obtained. Then, the conversion chart is switched to the density/toner attached amount conversion chart for the transparent toner. As a result, the gloss degree can be accurately predicted from the toner attached amount. Also, in the case of the white toner, the gloss degree can be accurately predicted from the toner attached amount by selecting the density/toner attached amount conversion chart for the white toner.

Although this invention has been described in detail with reference to certain embodiments, variations and modifications exist within the scope and spirit of the invention as described and defined in the following claims.

For example, while in the first embodiment, the image inspecting apparatus is connected to the image forming apparatus, the image inspecting apparatus may be included within the image forming apparatus. In this case, the image inspecting apparatus may be disposed at a stage subsequent to the fusing unit of the image forming apparatus. By installing the image inspecting apparatus at a predetermined position within the image forming apparatus, the gloss distribution of the image carrying medium on which an image is formed can be accurately inspected, so that the density distribution can also be inspected. Further, by feeding the result of inspection of the gloss distribution or the density distribution back to the image forming process, a high quality image can be formed on the image carrying medium.

The present application is based on Japanese Priority Application No. 2010-108198 filed May 10, 2010, the entire contents of which are hereby incorporated by reference.

What is claimed is:

1. An image inspecting apparatus comprising:
    a first light illuminating unit configured to apply light in a first direction to a measuring object on which an image is formed;
    a second light illuminating unit configured to apply light to the measuring object in a second direction different from the first direction;
    an imaging unit configured to receive specular light of the light applied to the measuring object from the first light illuminating unit, and diffused reflection light of the light applied to the measuring object from the second light illuminating unit; and
    an image inspecting unit configured to generate density distribution data of the image based on an amount of the diffused reflection light received by the imaging unit to inspect the image,
    wherein the image inspecting unit inspects a gloss distribution of the image by utilizing gloss reference data generated from the density distribution data and a gloss distribution of the image generated based on an amount of the specular light received by the imaging unit.

2. The image inspecting apparatus according to claim 1, wherein the image inspecting unit includes
    a density/toner attached amount converting unit configured to convert the density distribution data into a toner attached amount,
    a toner attached amount/gloss degree converting unit configured to generate the gloss reference data by converting the toner attached amount generated by the density/toner attached amount converting unit into a gloss degree, and by using a converting unit configured to calculate a target gloss degree from the toner attached amount,
    a gloss distribution generating unit configured to generate the gloss distribution of the image based on an amount of the specular light received by the imaging unit, and
    a gloss distribution inspection unit configured to determine the acceptability of the gloss distribution of the image by comparing the gloss reference data generated by the toner attached amount/gloss degree converting unit with the gloss distribution generated by the gloss distribution generating unit.

3. The image inspecting apparatus according to claim 2, wherein the image includes plural image-forming colors,
    wherein the density/toner attached amount converting unit is configured to convert the density distribution data into the toner attached amount for each of the image-forming colors,
    wherein the image inspecting unit further includes a toner attached amount totaling unit configured to calculate a total of the toner attached amounts of the image-forming colors,
    the toner attached amount/gloss degree converting unit generating the gloss reference data by converting the total of the toner attached amounts of the image-forming colors into the gloss degree.

4. The image inspecting apparatus according to claim 2, further comprising a plurality of the converting units,
    wherein the toner attached amount/gloss degree converting unit generates the gloss reference data by selecting one of the converting units depending on a condition,
    wherein the condition includes a fusing control condition for forming the image and a type of an image carrying medium used for forming the image.

5. The image inspecting apparatus according to claim 2, further comprising a plurality of the converting units,
    wherein the toner attached amount/gloss degree converting unit generates the gloss reference data by selecting one of the converting units depending on an image area of the print data.

6. The image inspecting apparatus according to claim 2, wherein the image inspecting unit includes an image area specifying unit configured to specify an image area to which no toner is attached based on the toner attached amount provided by the density/toner attached amount converting unit,
    wherein the gloss distribution inspection unit determines the acceptability of the gloss distribution of the image in the image area specified by the image area specifying unit in accordance with a determination standard different from a determination standard for another area.

7. The image inspecting apparatus according to claim 2, wherein the image includes at least one of a transparent toner image and a white toner image,
    wherein the density/toner attached amount converting unit converts into the toner attached amount the density distribution data of at least one of the transparent toner image and the white toner image, which density distribution data is generated based on distribution information of at least one of the transparent toner image and the white toner image that is included in the print data.

8. An image forming apparatus for forming an image on an image carrying medium,
    the image forming apparatus comprising the image inspecting apparatus according to claim 1,
    wherein the image inspecting apparatus is configured to inspect one or both of a gloss distribution and a density distribution of the image carrying medium as the measured object on which the image is formed.

9. An image inspecting method comprising:
    applying light in a first direction to a measuring object on which an image is formed, using a first light illuminating unit;
    applying light to the measuring object in a second direction different from the first direction, using a second light illuminating unit;
    receiving specular light of the light applied to the measured object in the first direction and diffused reflection light of the light applied to the measuring object in the second direction, using an imaging unit; and
    generating density distribution data of the image based on an amount of the received diffused reflection light received to inspect the image,
    wherein the image inspecting includes inspecting a gloss distribution of the image by utilizing gloss reference data generated from the density distribution data, and inspecting a gloss distribution of the image generated based on an amount of the specular light received.

10. The image inspecting method according to claim 9, wherein the image inspecting includes:

converting the density distribution data into a toner attached amount;

generating the gloss reference data by converting the toner attached amount into a gloss degree, by using a converting unit configured to calculate a target gloss degree from the toner attached amount;

generating the gloss distribution of the image based on an amount of the specular light received; and determining the acceptability of the gloss distribution of the image by comparing the gloss reference data generated with the gloss distribution generated.

11. The image inspecting method according to claim 10, wherein the image includes plural image-forming colors, wherein the converting includes converting the density distribution data into a toner attached amount for each of the image-forming colors, the image inspecting includes calculating a total of the toner attached amounts of the image-forming colors, and the toner attached amount/gloss degree inspecting includes generating the gloss reference data by converting the total of the toner attached amounts of the image-forming colors calculated into the gloss degree.

12. The image inspecting method according to claim 10, wherein the toner attached amount/gloss degree inspecting includes generating the gloss reference data by selecting one of a plurality of the converting units depending on a condition, wherein the condition includes a fusing control condition for forming the image and a type of an image carrying medium used for forming the image.

13. The image inspecting method according to claim 10, wherein the toner attached amount/gloss degree inspecting includes generating the gloss reference data by selecting one of a plurality of the converting units depending on an image area of the print data.

14. The image inspecting method according to claim 10, wherein the image inspecting includes an image area specifying step of specifying an image area to which no toner is attached based on the toner attached amount provided in the density/toner attached amount inspecting, wherein the determining includes determining the acceptability of the gloss distribution of the image in the image area specified in accordance with a determination standard different from a determination standard for another area.

15. The image inspecting method according to claim 10, wherein the image includes at least one of a transparent toner image and a white toner image, wherein the converting includes converting into the toner attached amount the density distribution data of at least one of the transparent toner image and the white toner image, which density distribution data is generated based on distribution information of at least one of the transparent toner image and the white toner image that is included in the print data.

16. A non-transitory computer-readable recording medium storing a program that causes a computer to perform the image inspecting method according to claim 9.

* * * * *